(12) United States Patent
Kottas et al.

(10) Patent No.: US 9,073,948 B2
(45) Date of Patent: Jul. 7, 2015

(54) AZABORINE COMPOUNDS AS HOST MATERIALS AND DOPANTS FOR PHOLEDS

(75) Inventors: Gregg Kottas, Ewing, NJ (US); Raymond C. Kwong, Plainsboro, NJ (US)

(73) Assignee: Universal Display Corporation, Ewing, NJ (US)

( * ) Notice: Subject to any disclaimer, the term of this patent is extended or adjusted under 35 U.S.C. 154(b) by 263 days.

(21) Appl. No.: 13/092,722

(22) Filed: Apr. 22, 2011

(65) Prior Publication Data

US 2011/0278556 A1 Nov. 17, 2011

Related U.S. Application Data

(63) Continuation-in-part of application No. 12/780,599, filed on May 14, 2010, now abandoned.

(51) Int. Cl.
*H01L 51/54* (2006.01)
*C07F 5/02* (2006.01)
*C09K 11/06* (2006.01)
*H01L 51/50* (2006.01)

(52) U.S. Cl.
CPC ............ *C07F 5/027* (2013.01); *C09K 11/06* (2013.01); *H01L 51/5012* (2013.01)

(58) Field of Classification Search
CPC .......... C07F 5/027; H01L 51/50; C09K 11/06
See application file for complete search history.

(56) References Cited

U.S. PATENT DOCUMENTS

| | | | |
|---|---|---|---|
| 4,769,292 A | 9/1988 | Tang et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 7,279,704 B2 | 10/2007 | Walters et al. |
| 7,431,968 B1 | 10/2008 | Shtein et al. |

(Continued)

FOREIGN PATENT DOCUMENTS

| | | |
|---|---|---|
| JP | 2001093670 | 4/2001 |
| JP | 2003234192 | 8/2003 |
| JP | 2004 253298 | 9/2004 |

OTHER PUBLICATIONS

Agou et al., Chemical Communications, (2009), (14), pp. 1894-1896.

(Continued)

*Primary Examiner* — Dawn L. Garrett
(74) *Attorney, Agent, or Firm* — Duane Morris LLP

(57) ABSTRACT

Novel organic compounds comprising azaborine are provided. In particular, the compounds comprise a dibenzo-1,4,-azaborine core having a phenyl substituent on the boron atom, and aryl or heteroaryl substituents at positions 2 and 6 of the phenyl substituent. These compounds may be advantageously used in organic light-emitting devices to provide improved efficiency and lifetime.

18 Claims, 6 Drawing Sheets

(56) References Cited

U.S. PATENT DOCUMENTS

| | | |
|---|---|---|
| 2003/0157366 A1 | 8/2003 | Matsuura et al. |
| 2003/0230980 A1 | 12/2003 | Forrest et al. |
| 2004/0174116 A1 | 9/2004 | Lu et al. |
| 2011/0278556 A1 | 11/2011 | Kottas et al. |

OTHER PUBLICATIONS

Agou et al., Chemical Communications, (2007), (30), pp. 3204-3206.
Agou et al., Chemistry—A European Journal, (2009), vol. 15, No. 20, pp. 5056-5062.
Agou et al., Organic Letters, (2009), vol. 11, No. 16, pp. 3534-3537.
Maitlis, Journal of the Chemical Society, (1961) pp. 425-429.
Krantz et al., Journal of the Chemical Society, Chemical Communications, (1992), (17), pp. 1247-1248.
Baldo et al., "Highly Efficient Phosphorescent Emission from Organic Electroluminescent Devices," Nature, vol. 395, 151-154, (1998).
Baldo et al., "Very high-efficiency green organic light-emitting devices based on electrophosphorescence," Appl. Phys. Lett., vol. 75, No. 3, 4-6 (1999).
U.S. Appl. No. 12/780,599, filed May 14, 2010.
Shi et al., "Anthracene derivatives for stable blue-emitting organic electroluminescence devices" Appl. Phys. Lett., vol. 80, No. 17, p. 3201, Apr. 29, 2002.
Daku et al., "Investigation of the reduced high-potential iron-sulfur protein from *Chromatium vinosum* and relevant model compounds: a unified picture of the electronic structure of $[Fe_4S_4]^{+2}$ systems through magnetic and optical studies" Inorg. Chem. 2003, 42, 6824.
Agou et al., "Syntheses, structure and optical properties of ladder-type fused azaborines" Org. Lett. 2006, vol. 8, No. 11, 2241.
Gilman et al., "Synthesis of some 5,10-dihydrophenazasilene derivatives" J. Org. Chem. Jun. 1961, 2013.
Spivey et al., "Concise synthesis, preparative resolution, absolute configuration determination, and applications of an atropisomeric biaryl catalyst for asymmetric acylation" J. Org. Chem. 2003, 68, 7379.
Office Action and Search Report issued Aug. 6, 2014 for corresponding Chinese Application No. 201180023920.X.
Office Action and Search Report issued Sep. 17, 2014 for corresponding Taiwanese Application No. 100117132.
Cuihua, Zhao et al., "Optoelectronic Materials of Organoboron II-Conjugated Systems," Progress in Chemistry, vol. 21, No. 12, Dec. 24, 2009, p. 2605-2611 (English Abstract Provided).
Notice of Reasons of Rejection dated Sep. 29, 2014 issued for corresponding Japanese Patent Application No. 2013-510340.

AZABORINE COMPOUNDS AS HOST MATERIALS AND DOPANTS FOR PHOLEDS

This application is a continuation-in-part of U.S. patent application Ser. No. 12/780,599, filed May 14, 2010, the entire disclosure of which is incorporated by reference herein.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel organic compounds that may be advantageously used in organic light-emitting devices (OLEDs). More particularly, the invention relates to dibenzo-1,4-azaborine compounds containing aryl or heteroaryl substituents and their use in PHOLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light-emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entireties.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the structure:

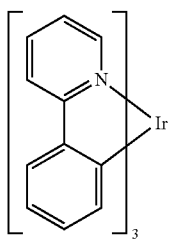

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Azaborine compounds are provided, the compounds comprising the formula:

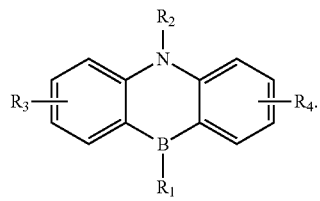

Formula I $R_1$ is a group containing two or more aryl or heteroaryl groups, and the aryl or heteroaryl groups are conjugated or fused. $R_3$ and $R_4$ may represent mono, di, tri, tetra, or penta substitutions. $R_2$, $R_3$ and $R_4$ are independently selected from hydrogen, alkyl, alkoxy, amino, alkenyl, alkynyl, aryl, and heteroaryl. Preferably, $R_2$ includes an aryl or a heteroaryl.

In one aspect, the compound comprises the formula:

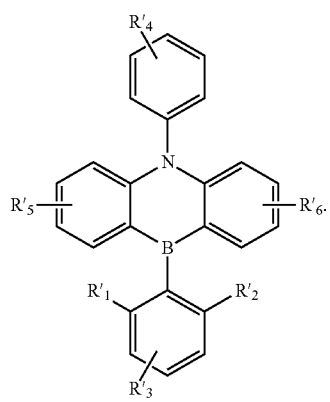

Formula II $R'_3$, $R'_5$, and $R'_6$ may represent mono, di, tri, tetra, or penta substitutions. $R'_1$, $R'_2$, $R'_3$, $R'_4$, $R'_5$ and $R'_6$ are independently selected from hydrogen, alkyl, alkoxy, amino, alkenyl, alkynyl, aryl, and heteroaryl. At least one of $R'_1$ and $R_2$ is an aryl or heteroaryl and the aryl or heteroaryl groups are conjugated or fused.

In one aspect, $R'_3$, $R'_4$, $R'_5$, and $R'_6$ are independently aryl or heteroaryl.

In another aspect, $R'_4$ includes aryl or heteroaryl substitutions positioned ortho to the carbon atom in the aryl or heteroaryl group that is connected to the nitrogen atom.

Specific examples of azaborine compounds are provided. In one aspect, the compounds are selected from the group consisting of:

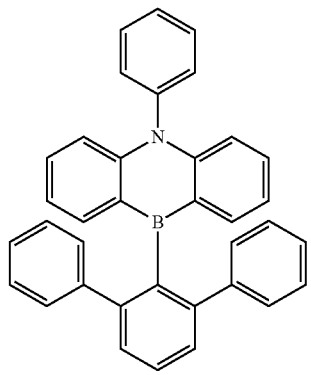 [SMILES: c1ccc(-c2cccc(-c3ccccc3)c2B2c3ccccc3N(c3ccccc3)c3ccccc32)cc1]

Compound 1

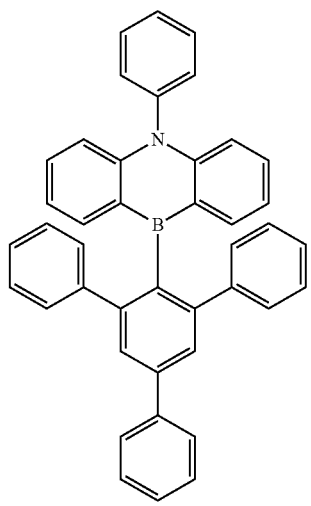 [SMILES: c1ccc(-c2cc(-c3ccccc3)c(B3c4ccccc4N(c4ccccc4)c4ccccc43)c(-c3ccccc3)c2)cc1]

Compound 2

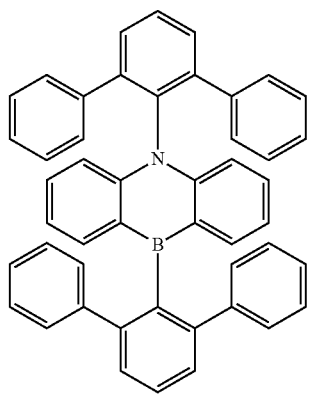

Compound 3

Compound 4
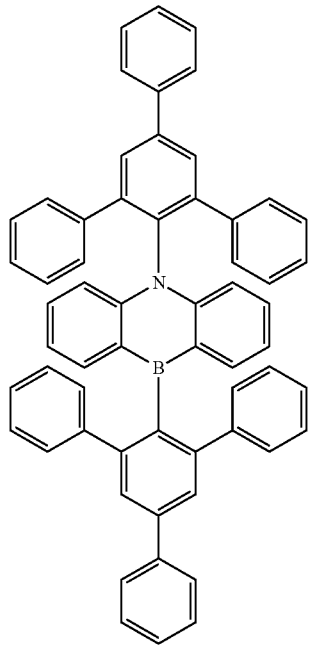
Compound 5
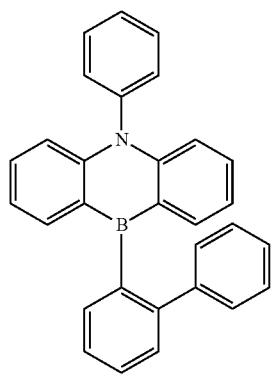
Compound 6
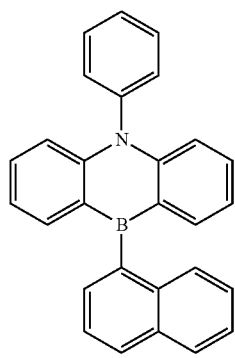
Compound 7
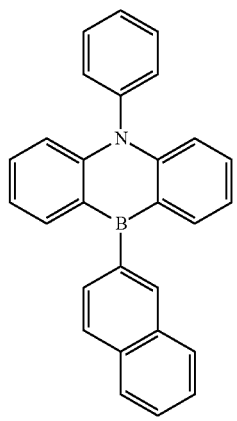
Compound 8
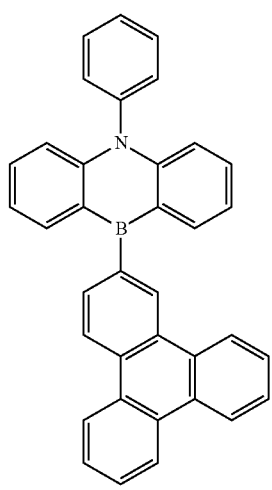
Compound 9
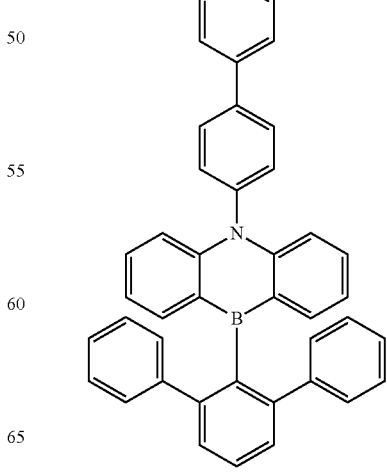

Compound 10
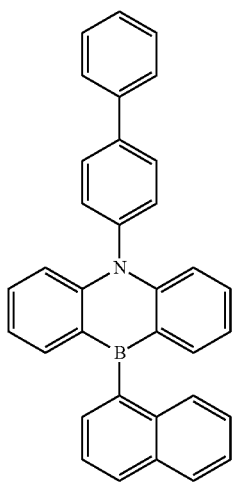
Compound 11
Compound 12
Compound 13
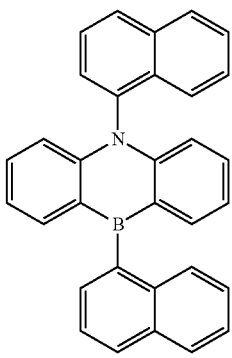
Compound 14
Compound 15
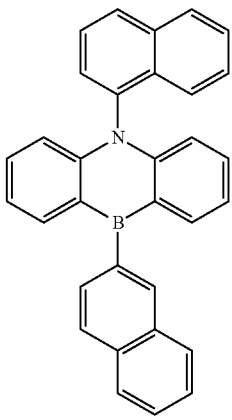
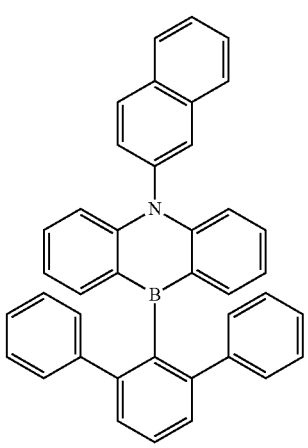
Compound 16
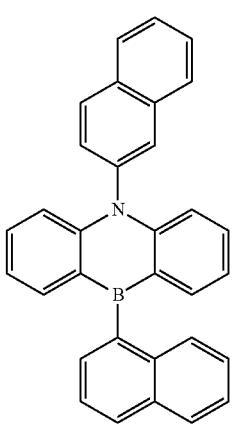

Compound 17
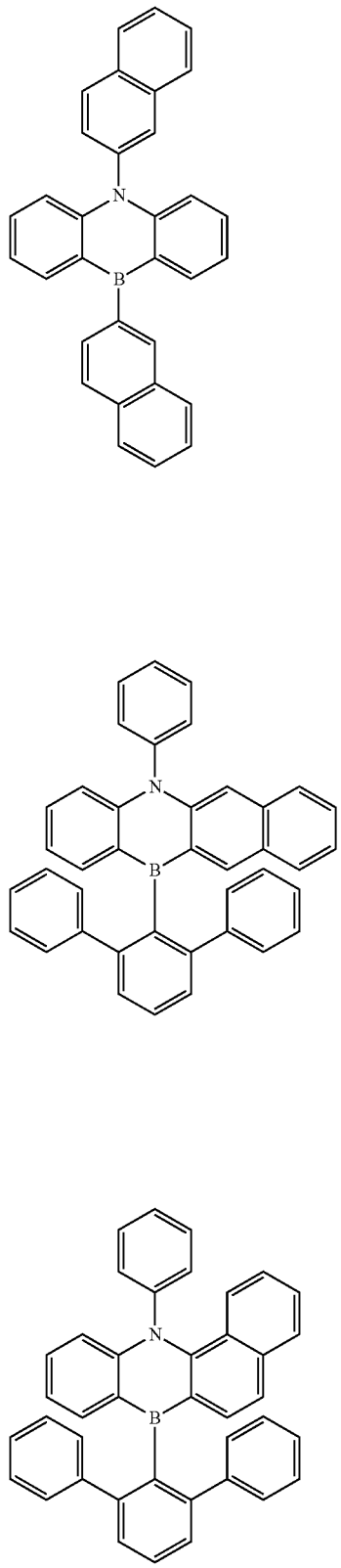
Compound 18
Compound 19
Compound 20
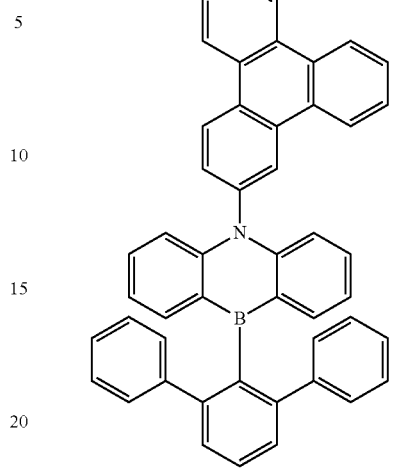
Compound 21
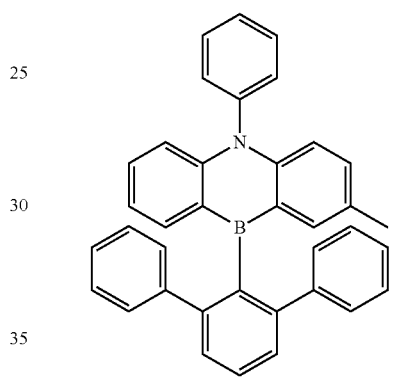
Compound 22
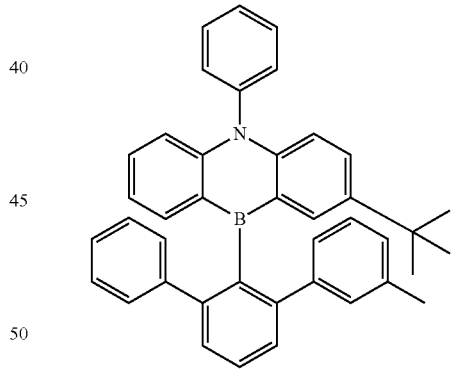
Compound 23
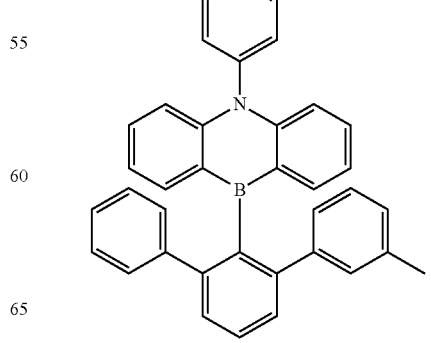

Compound 24
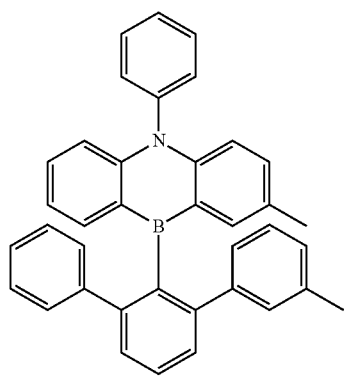
Compound 25
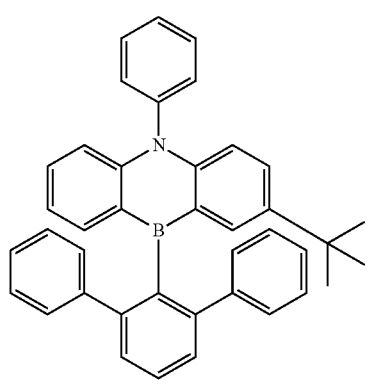
Compound 26
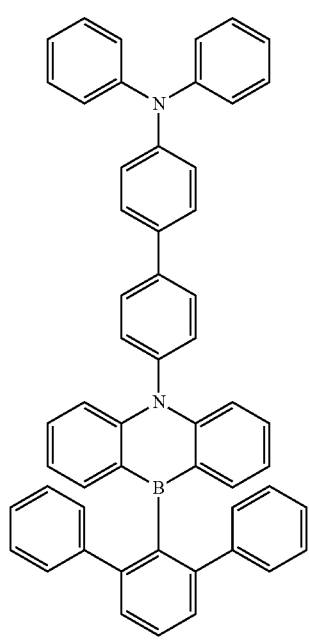
Compound 27
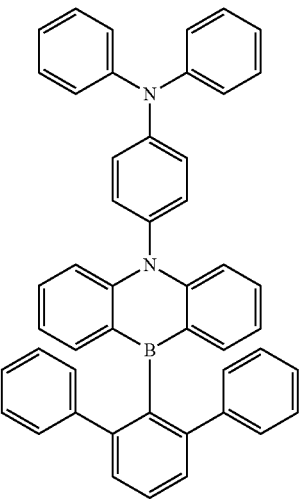
Compound 28
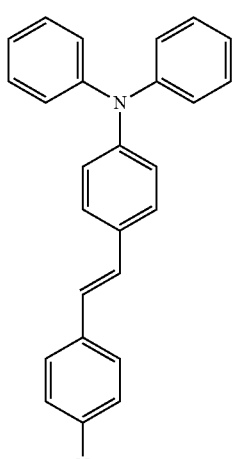
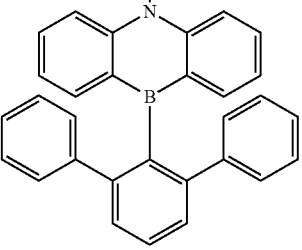
Compound 29
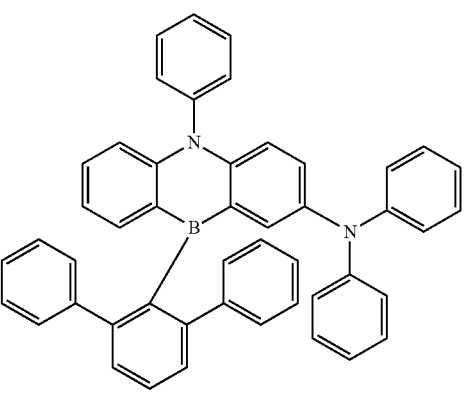

Compound 30
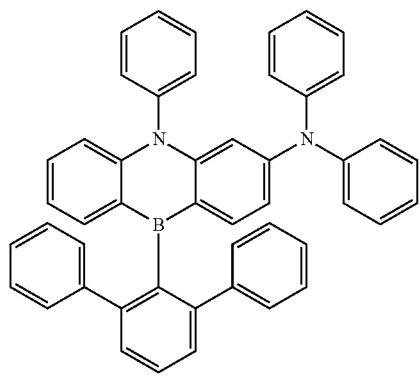
Compound 33
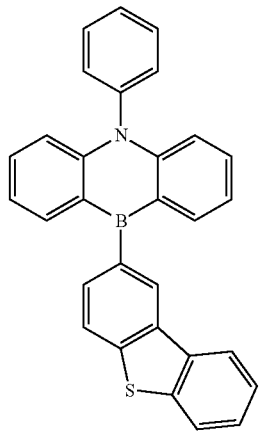
Compound 31
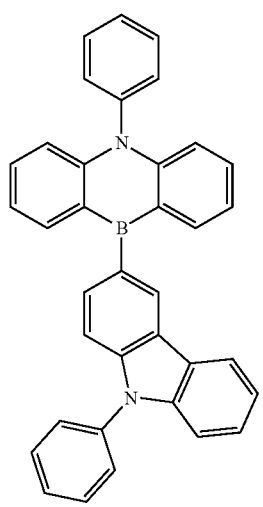
Compound 34
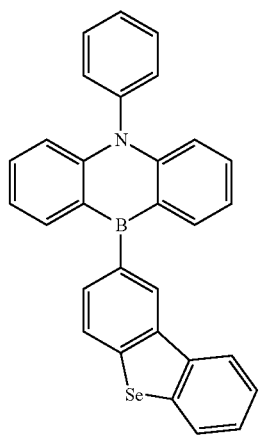
Compound 32
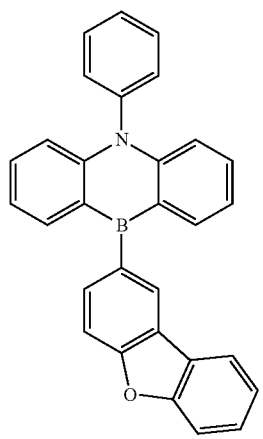
Compound 35
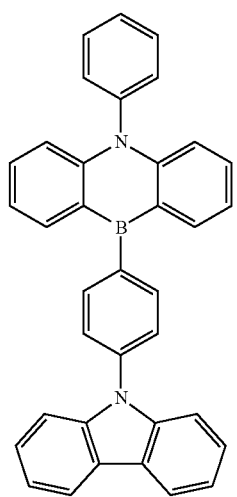

Compound 36
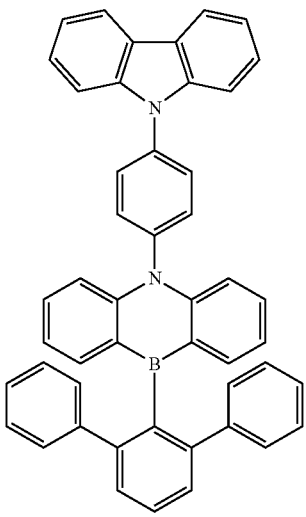
Compound 37
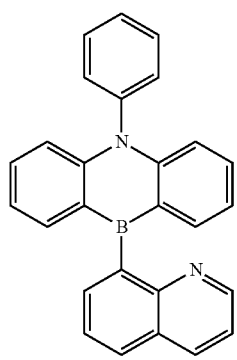
Compound 38
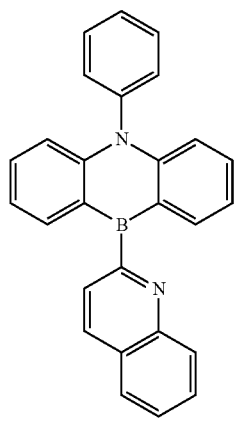
Compound 39
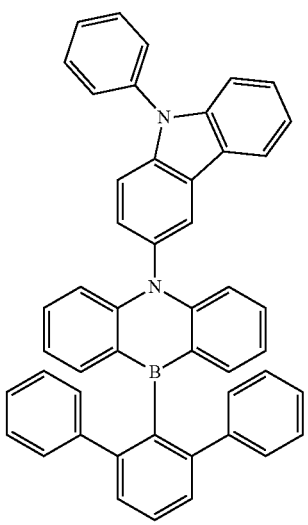
Compound 40
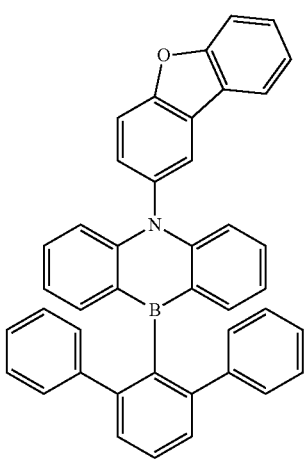
Compound 41
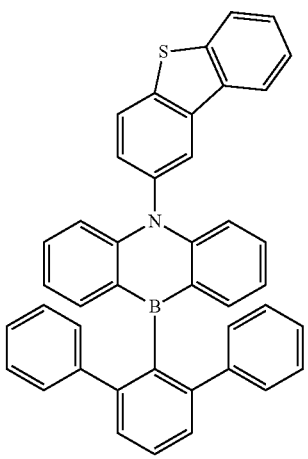

-continued
Compound 42
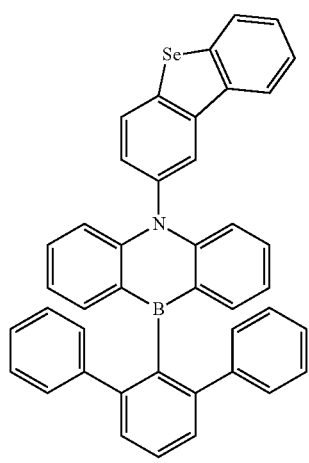
Compound 43
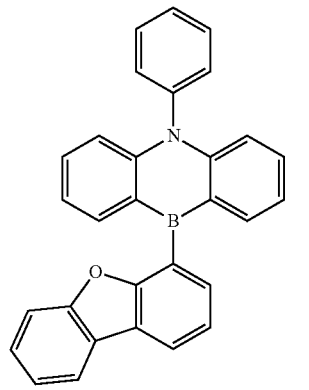
Compound 44
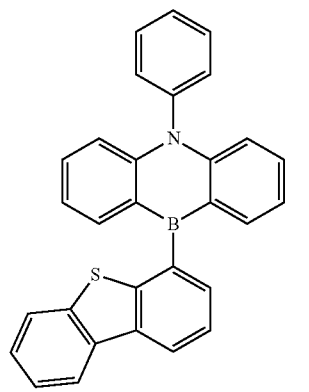
Compound 45
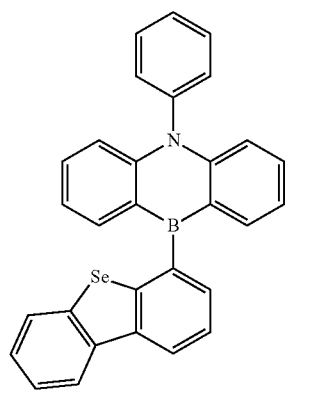
-continued
Compound 46
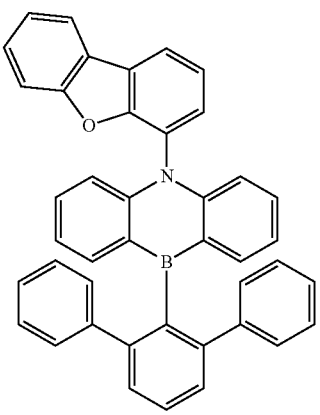
Compound 47
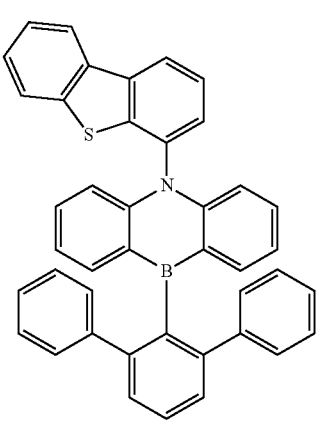
Compound 48
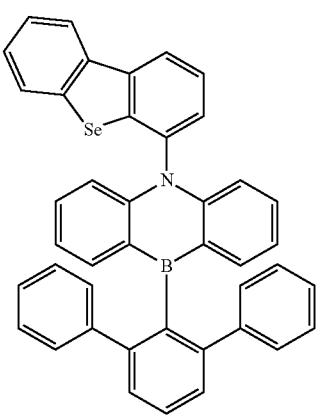
In another aspect, the compounds are selected from the group consisting of:

Compound 49
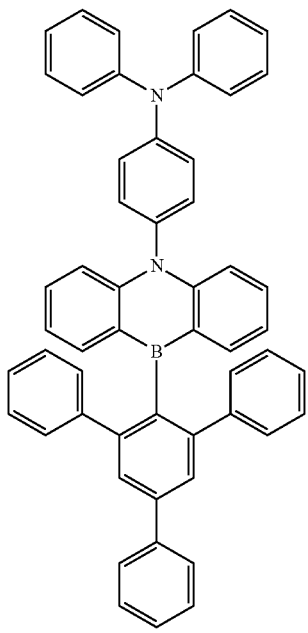
Compound 50
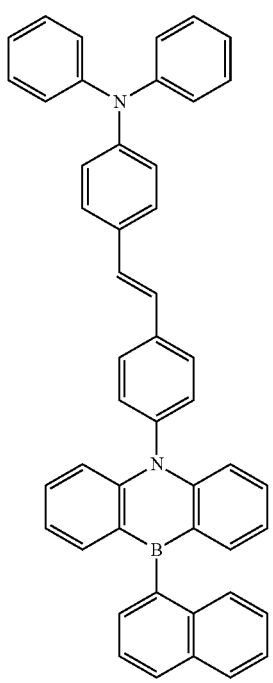
Compound 51
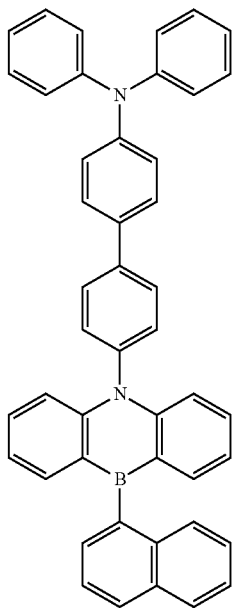
Compound 52
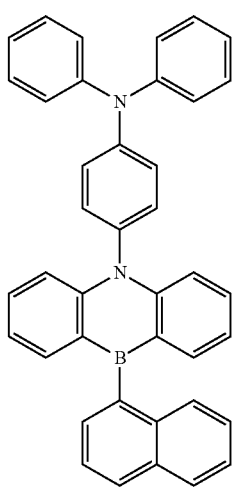
Compound 53

Compound 54
Compound 55
Compound 56
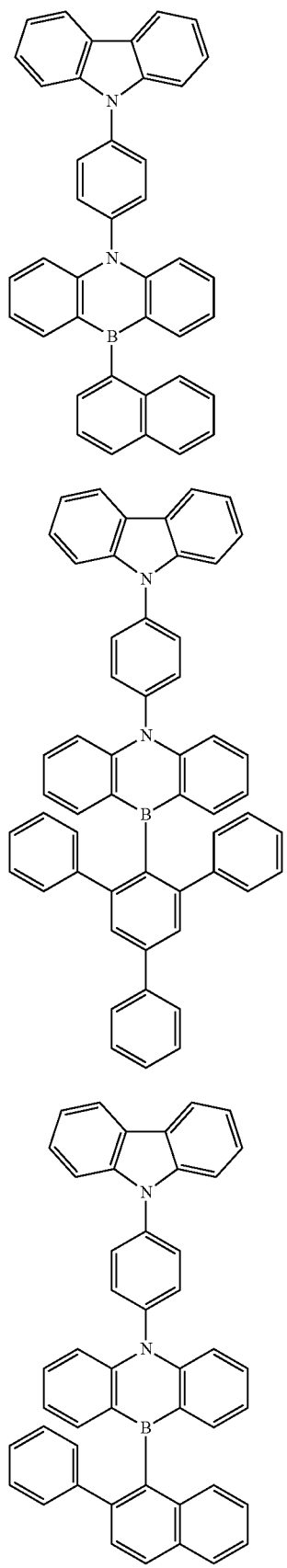
Compound 57
Compound 58
Compound 59
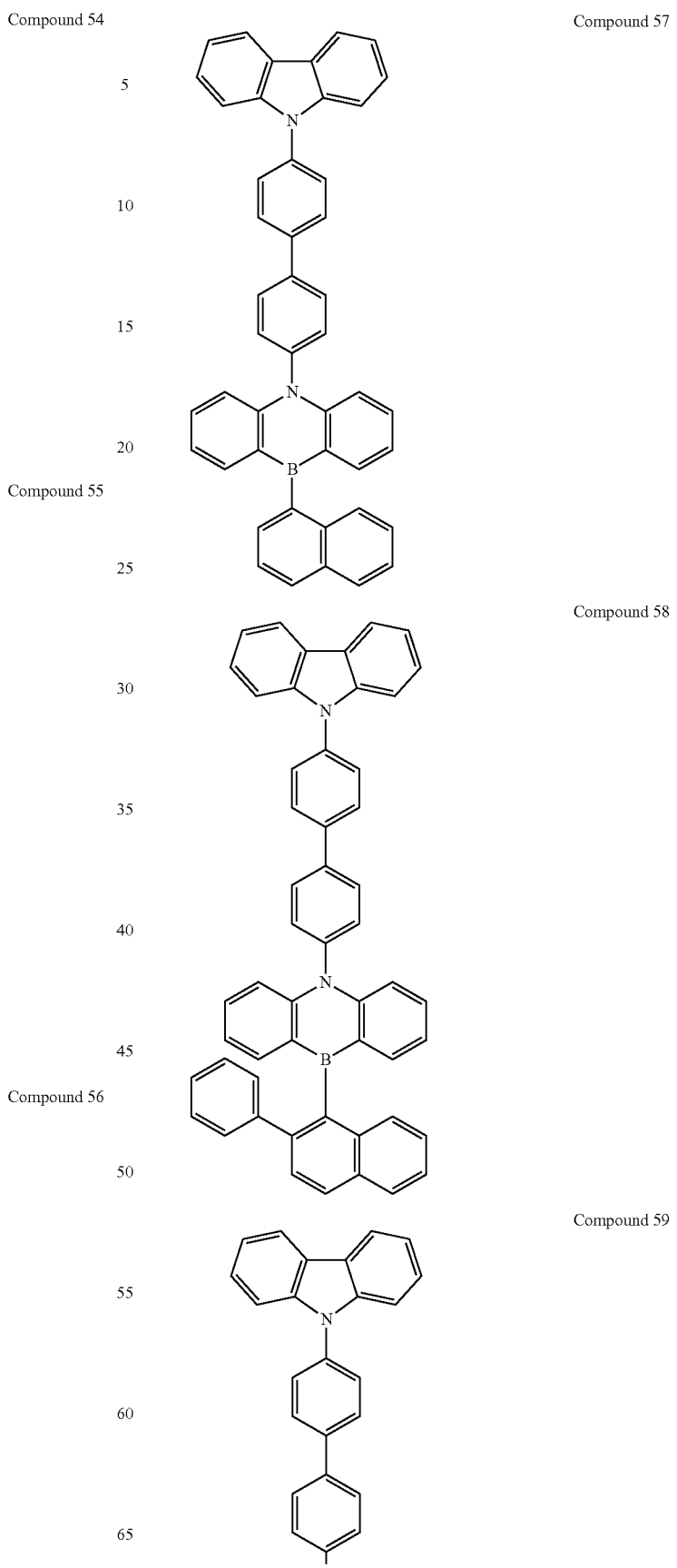

-continued

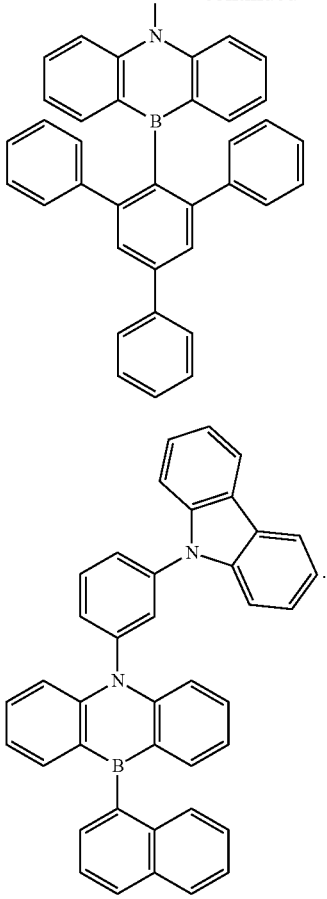

Compound 60

Additionally, a first device comprising an organic light-emitting device is provided. The organic light-emitting device comprises an anode, a cathode, and an organic layer, disposed between the anode and the cathode, and the organic layer further comprises a compound comprising Formula I, as described above.

$R_1$ is a group containing two or more aryl or heteroaryl groups, and the aryl or heteroaryl groups are conjugated or fused. $R_3$ and $R_4$ may represent mono, di, tri, tetra, or penta substitutions. $R_2$, $R_3$ and $R_4$ are independently selected from hydrogen, alkyl, alkoxy, amino, alkenyl, alkynyl, aryl, and heteroaryl. Preferably, $R_2$ includes an aryl or a heteroaryl.

In one aspect, the compound comprises Formula II.

$R'_3$, $R'_4$, $R'_5$, and $R_6$ may represent mono, di, tri, tetra, or penta substitutions. $R'_1$, $R'_2$, $R'_3$, $R'_4$, $R'_5$ and $R'_6$ are independently selected from hydrogen, alkyl, alkoxy, amino, alkenyl, alkynyl, aryl, and heteroaryl. At least one of $R'_1$ and $R_2$ is an aryl or heteroaryl, and the aryl or heteroaryl groups are conjugated or fused.

In one aspect, $R'_3$, $R'_4$, $R'_5$, and $R'_6$ are independently aryl or heteroaryl.

In another aspect, $R'_4$ includes aryl or heteroaryl substitutions positioned ortho to the carbon atom in the aryl or heteroaryl group that is connected to the nitrogen atom.

Specific examples of azaborine compounds that may be used in the devices are provided, and include compound selected from the group consisting of Compounds 1-48. In another aspect, azaborine compounds that may be used in the devices are provided, and include compound selected from the group consisting of Compounds 49-60.

In one aspect, the organic layer is a blocking layer and the compound having Formula is a blocking material.

In another aspect, the organic layer is an emissive layer and the compound comprising Formula I is a host. The organic layer may further comprise an emissive dopant. In yet another aspect, the organic layer is an emissive layer and the compound comprising Formula I is a fluorescent emitter.

In one aspect, the first device is a consumer product. In another aspect, the first device is an organic light-emitting device.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, pp. 151-154, 1998; ("Baldo-I") and Baldo et al., "Very high-efficiency green organic light-emitting devices based on electrophosphorescence," Appl. Phys. Lett., vol. 75, No. 3, pp. 4-6, 1999 ("Baldo-II"), which are incorporated by reference in their entireties. Phosphorescence is described in more detail in U.S. Pat. No. 7,279,704 at cols. 5-6, which are incorporated by reference.

Figure 1:
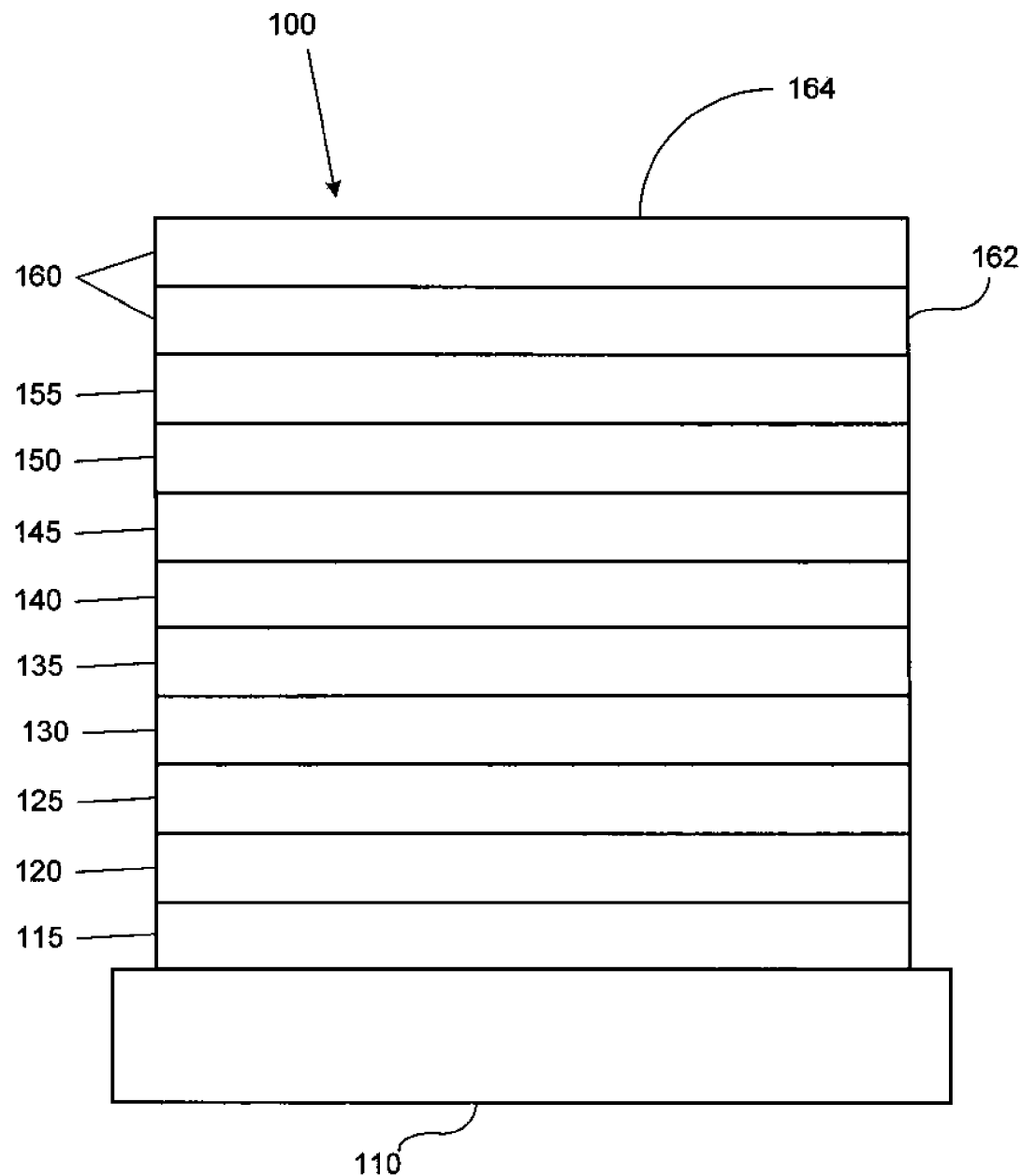
FIG. 1 shows an organic light-emitting device.

FIG. 1 shows an organic light-emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F.sub.4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
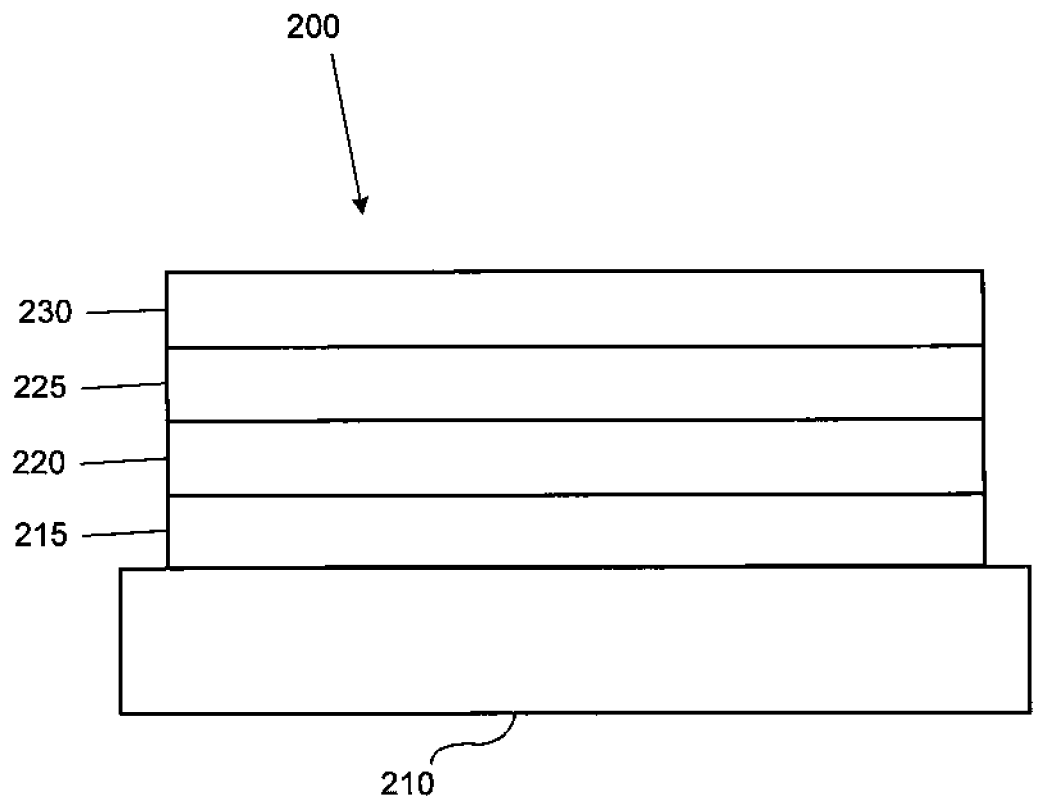
FIG. 2 shows an inverted organic light-emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures.

More generally, organic devices, such as organic transistors, may employ the materials and structures.

The terms halo, halogen, alkyl, cycloalkyl, alkenyl, alkynyl, heterocyclic group, aryl, aromatic group, and heteroaryl are known to the art, and are defined in U.S. Pat. No. 7,279,704 at cols. 31-32, which are incorporated herein by reference.

Figure 3:
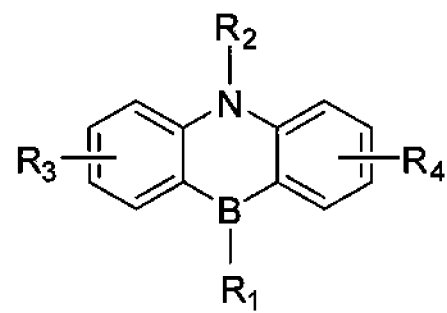
FIG. 3 shows an azaborine compound.

Novel azaborine compounds are provided that may be used as host materials or fluorescent emissive dopant material in organic light-emitting devices (illustrated in FIG. 3). 1,4-azaborine compounds are particularly interesting heteroaromatic molecules because of the boron and nitrogen heteroatoms in the core of the compound. These 1,4-azaborine compounds can display high singlet and triplet energies due to the lack of conjugation relative to their all-carbon congeners, and they are bright blue fluorescent emitters.

Anthracene derivatives and organic devices containing these compounds have been reported in the literature, but the known compounds have several problems that may limit their use in OLEDs. Anthracene is a highly conjugated polyaromatic hydrocarbon. OLEDs with anthracene derivatives as the host materials, such as 9,10-di-(2-naphthyl)anthracene, can have long device lifetimes. (See, Appl. Phys. Lett., Vol. 80, p. 3201 2002). However, the triplet energy of anthracene is very low (680 nm), due to the high conjugation, making it unsuitable as a host material for OLEDs with phosphorescent emitters in the visible region. Dibenzo-1,4-azaborine is isolelectronic to anthracene. The center azaborine ring is semi-aromatic, so the degree of conjugation may be reduced and the triplet energy may be higher compared to anthracene. Therefore, azaborine compounds may be advantageously used to raise the triplet energy of the host.

1,4-azaborine compounds have been reported in the literature (see, US 2003/0157366). However, these trivalent boron compounds can be chemically unstable because the electron deficiency of the boron atom makes it susceptible to nucleophilic attack. Without being bound by theory, it is believed that the boron atom may still need to be protected to minimize chemical instability despite the semi-aromatic character of the center ring in dibenzo-1,4-azaborine. HOMO, LUMO and lowest triplet energy ($T_1$), as calculated by DFT (Gaussian/B31yp/cep-31g), of some dibenzo-1,4-azaborine compounds are shown in Table 1.

TABLE 1

| Structure | HOMO (eV) | LUMO (eV) | Gap (eV) | Dipole (D) | $T_1$ (nm) |
|---|---|---|---|---|---|
| 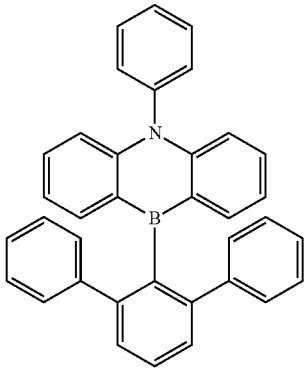 Compound 1 | −5.29 | −1.31 | −3.98 | 3.52 | 449 |
| 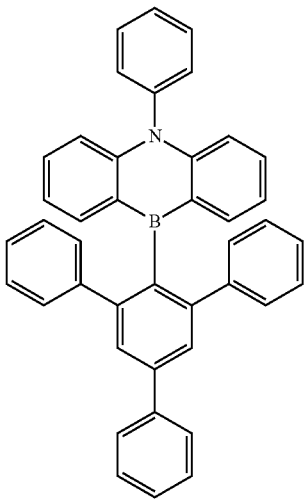 Compound 2 | −5.3 | −1.34 | −3.96 | 3.73 | 450 |

TABLE 1-continued
| Structure | HOMO (eV) | LUMO (eV) | Gap (eV) | Dipole (D) | $T_1$ (nm) |
| --- | --- | --- | --- | --- | --- |
| 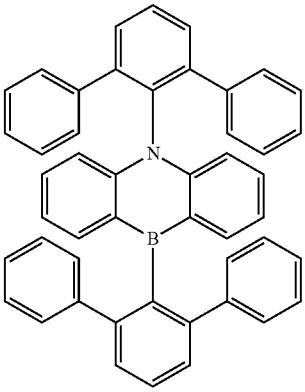 [SMILES: c1ccc(-c2cccc(-c3ccccc3)c2B2c3ccccc3N(c3c(-c4ccccc4)cccc3-c3ccccc3)c3ccccc32)cc1]  Compound 3 | −5.32 | −1.32 | −3.99 | 2.88 | 447 |
| 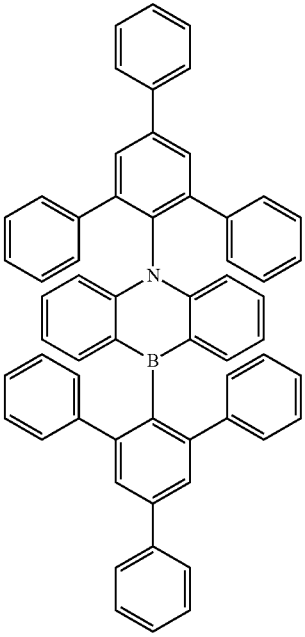 [SMILES: c1ccc(-c2cc(-c3ccccc3)c(B3c4ccccc4N(c4c(-c5ccccc5)cc(-c5ccccc5)cc4-c4ccccc4)c4ccccc43)c(-c3ccccc3)c2)cc1]  Compound 4 | −5.32 | −1.34 | −3.98 | 3.43 | 448 |
| 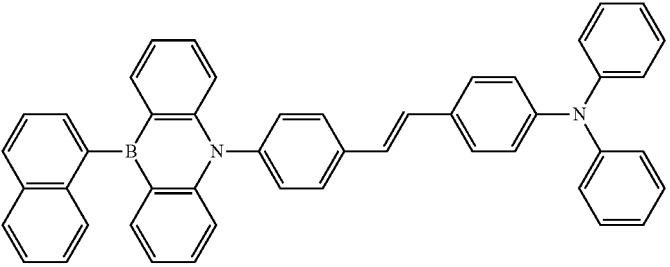 [SMILES: C(=C\c1ccc(N2c3ccccc3B(c3cccc4ccccc34)c3ccccc32)cc1)/c1ccc(N(c2ccccc2)c2ccccc2)cc1]  Compound 50 | −5.00 | −1.63 | −3.37 | 5.95 | 596 |

TABLE 1-continued
| Structure | HOMO (eV) | LUMO (eV) | Gap (eV) | Dipole (D) | $T_1$ (nm) |
|---|---|---|---|---|---|
| 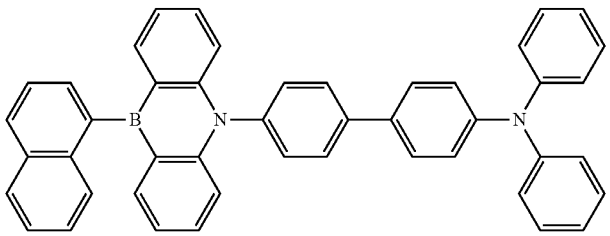 [SMILES: c1ccc(N(c2ccccc2)c2ccc(-c3ccc(N4c5ccccc5B(c5cccc6ccccc56)c5ccccc54)cc3)cc2)cc1]  Compound 51 | −5.10 | −1.32 | −3.79 | 5.12 | 462 |
| 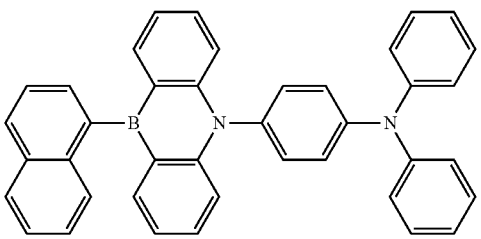 [SMILES: c1ccc(N(c2ccccc2)c2ccc(N3c4ccccc4B(c4cccc5ccccc45)c4ccccc43)cc2)cc1]  Compound 52 | −5.28 | −1.30 | −3.97 | 4.87 | 462 |
| 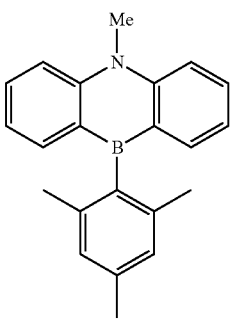 [SMILES: Cc1cc(C)c(B2c3ccccc3N(C)c3ccccc32)c(C)c1]  Compound X | −5.44 | −1.38 | −4.06 | 3.02 | 443 |
| 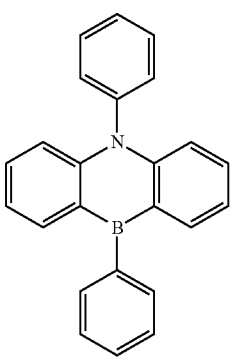 [SMILES: c1ccc(B2c3ccccc3N(c3ccccc3)c3ccccc32)cc1]  Compound Y | −5.35 | −1.33 | 4.02 | 3.43 | 447 |

TABLE 1-continued

| Structure | HOMO (eV) | LUMO (eV) | Gap (eV) | Dipole (D) | $T_1$ (nm) |
|---|---|---|---|---|---|
| 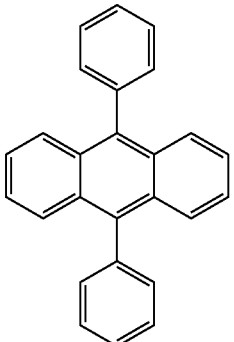 Compound Z | −5.09 | −1.6 | −3.48 | 0 | 717 |

Additionally, the calculated triplet energies for 1,4-azaborine compounds are much high than the values measured for 9,10-diphenylanthracene (Compound Z). Comparing the HOMO, LUMO and $T_1$ of the dibenzo-1,4-azaborine compounds and Ir(ppy)$_3$, it is believed that the dibenzo-1,4-azaborine compounds provided herein can work as a host for Ir(ppy)$_3$ in phosphorescent OLEDs.

It is believed that the dibenzo-1,4-azaborine compounds provided herein may be advantageously used over known azaborine compounds for several reasons. First, without being bound by theory, it is believed that substituents at the 2 and 6 positions of the phenyl attached to the boron atom provide steric protection to the boron atom. In particular, Compound Y, which has an unsubstituted phenyl attached to the boron, shows signs of decomposition during the PL measurement in solution whereas Compound 2, which has 2,4,6-triphenylphenyl attached to the boron, do not show signs of decomposition. Secondly, the substituent $R_1$ at the boron may have the least conjugation to the 1,4-azaborine system. This feature may allow an independent electronically and/or photophysically active group, preferably with 2 or more aryl or heteroaryl groups that are conjugated or fused, to be connected to the 1,4-azaborine system for tuning the electronic and/or photophysical properties. For example, if a $R_1$ is 2-quinoline, the 2-quinoline group can provide a relatively low LUMO which may facilitate electron transport and stabilization of negative charge. Some groups may be able to provide steric protection to the boron atom and electronic and/or photophysical tuning simultaneously. For example, if $R_1$ is phenyl and its 2,6 positions are further substituted by aryl or heteroaryl groups, the boron atom is sterically protected, and the 2,6-diphenylphenyl moiety provides a biphenyl conjugation. If $R_1$ is 1-naphthyl, the boron atom is partially sterically protected and the naphthyl group provides extra conjugation. In addition to further conjugation and stabilization of charges, the aryl or heteroaryl substituents, preferably with 2 or more aryl or heteroaryl groups that are conjugated or fused, may provide high glass transition temperatures and suitable evaporation temperatures. For example, previously reported Compound X, which has 2,4,6-trimethylphenyl attached to the boron, compared to Compound 2, may provide low glass transition temperatures and evaporation temperatures too low for device fabrication by vacuum processes because the 2,6-methyl substituents of Compound X do not provide a high enough molecular weight. If higher molecular weight alkyl groups are used, the compound may melt too easily; and may have poor electronic properties for devices due to too many non-electronically active alkyl groups. Therefore, the dibenzo-1,4-azaborine compounds provided herein are particularly desirable and may be advantageously used to provide devices with improved stability.

Figure 4:
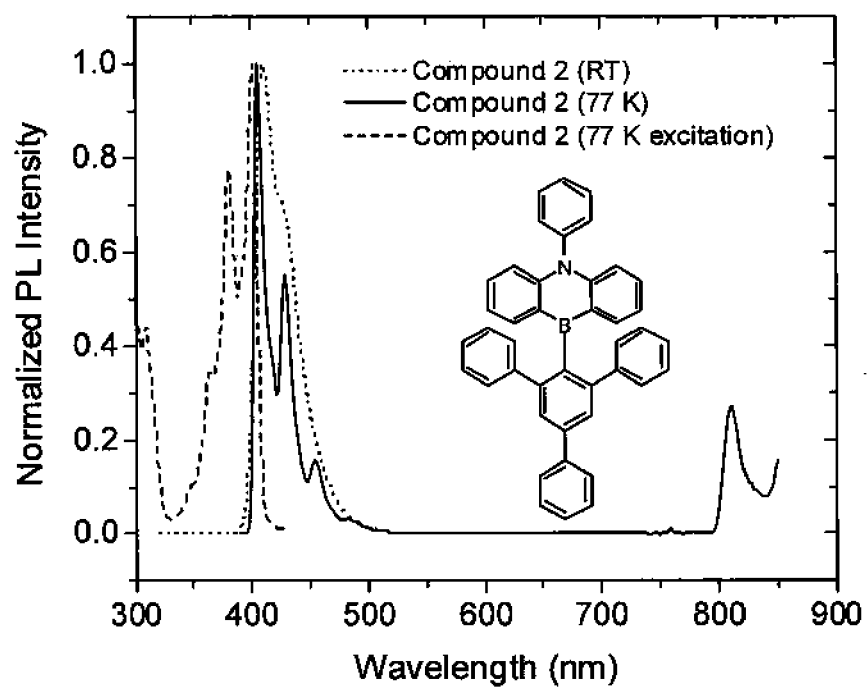
FIG. 4 shows the photoluminescence spectra of Compound 2.
Figure 5:
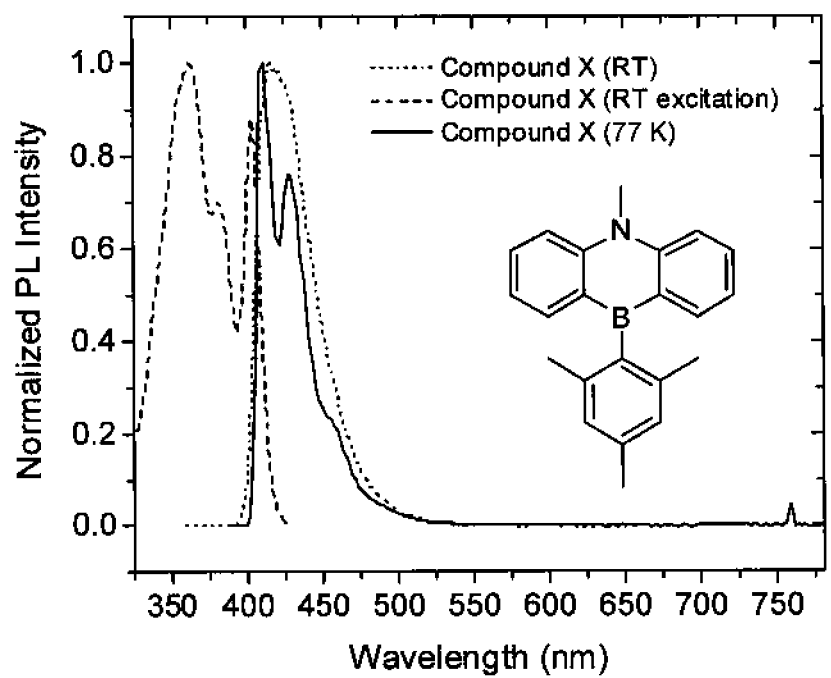
FIG. 5 shows the photoluminescence spectra of Compound X.
Figure 6:
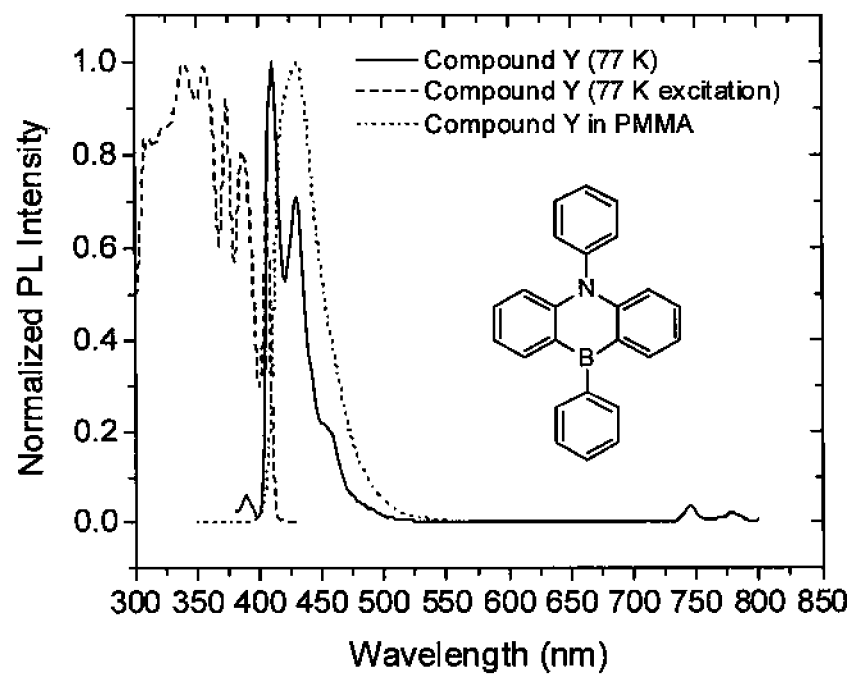
FIG. 6 shows the photoluminescence spectra of Compound Y.

In addition, the azaborine compounds provided may be used as fluorescent emitting materials. The dibenzo-1,4,-azaborine compounds provided herein demonstrate high energy emission, i.e., 400-450 nm, similar to the fluorescence measured for anthracene. For example, the photoluminescence spectra of Compound 2, Compound X and Compound Y are shown in FIGS. 4-6. At 77 K, a low energy emission (>700 nm) is observed in Compound 2 and Compound Y, but not Compound X. The low energy emission may be the phosphorescence of Compound 2 and Compound Y, however, the value significantly deviates from the DFT calculation. While the phosphorescence emission from high energy is expected to be quenched, the phosphorescence of Ir(ppy)$_3$ type compounds is not quenched by Compound 2 using thin film PL experiments. In devices, the efficiency of the device using Compound B as the host with Compound A, an Ir(ppy)$_3$ type compound, as the dopant, is comparable to a standard device using CSP as the host.

Furthermore, the azaborine compounds provided show an intense deep blue fluorescence (~410 nm). In particular, a thin film of Compound 2 shows a PLQY of 64%. Therefore, the compounds provided may be desirable for use as fluorescent emitters in OLEDs.

Azaborine compounds are provided, the compounds comprising the formula:

Formula I

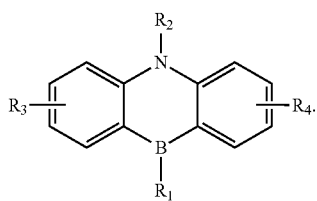

R₁ is a group containing two or more aryl or heteroaryl groups, and the aryl or heteroaryl groups are conjugated or fused. $R_3$ and $R_4$ may represent mono, di, tri, tetra, or penta substitutions. $R_2$, $R_3$ and $R_4$ are independently selected from hydrogen, alkyl, alkoxy, amino, alkenyl, alkynyl, aryl, and heteroaryl. Preferably, $R_2$ includes an aryl or a heteroaryl.

In one aspect, the compound comprises the formula:

Formula II

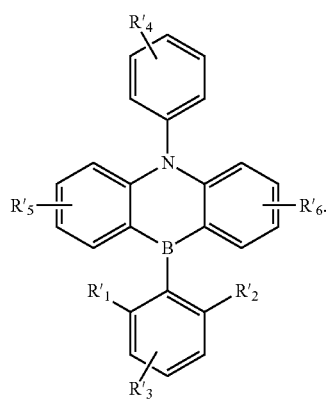

$R'_3$, $R'_4$, $R'_5$, and $R'_6$ may represent mono, di, tri, tetra, or penta substitutions. $R'_1$, $R'_2$, $R'_3$, $R_4$, $R'_5$ and $R'_6$ are independently selected from hydrogen, alkyl, alkoxy, amino, alkenyl, alkynyl, aryl, and heteroaryl. At least one of and $R_2$ is an aryl or heteroaryl and the aryl or heteroaryl groups are conjugated or fused.

In one aspect, $R'_3$, $R'_4$, $R'_5$, and $R'_6$ are independently aryl or heteroaryl.

In another aspect, $R'_4$ includes aryl or heteroaryl substitutions positioned ortho to the carbon atom in the aryl or heteroaryl group that is connected to the nitrogen atom.

Specific examples of azaborine compounds are provided and include compounds selected from the group consisting of:

Compound 1

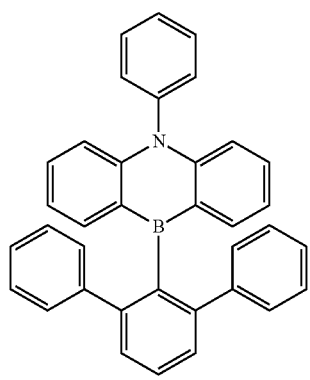

Compound 2

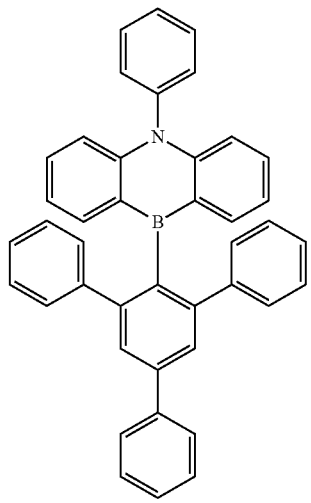

Compound 3

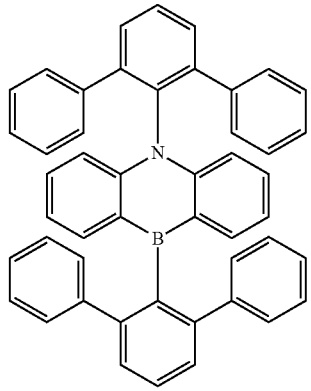

Compound 4

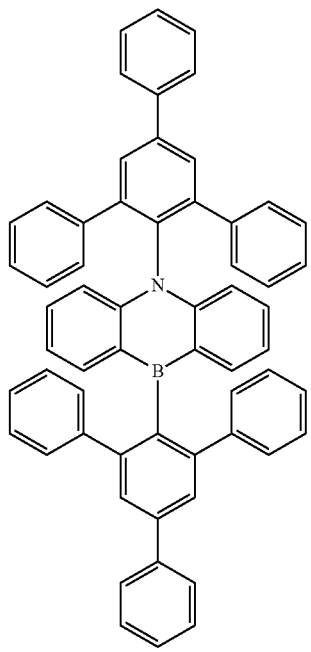

Compound 5
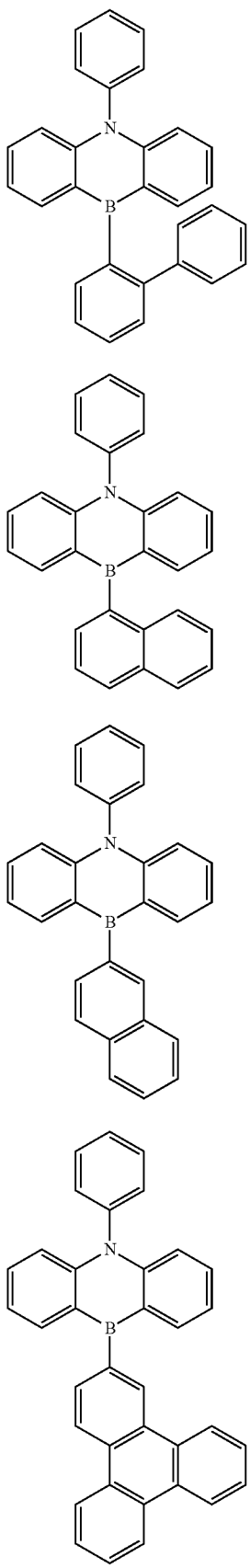
Compound 6
Compound 7
Compound 8
Compound 9
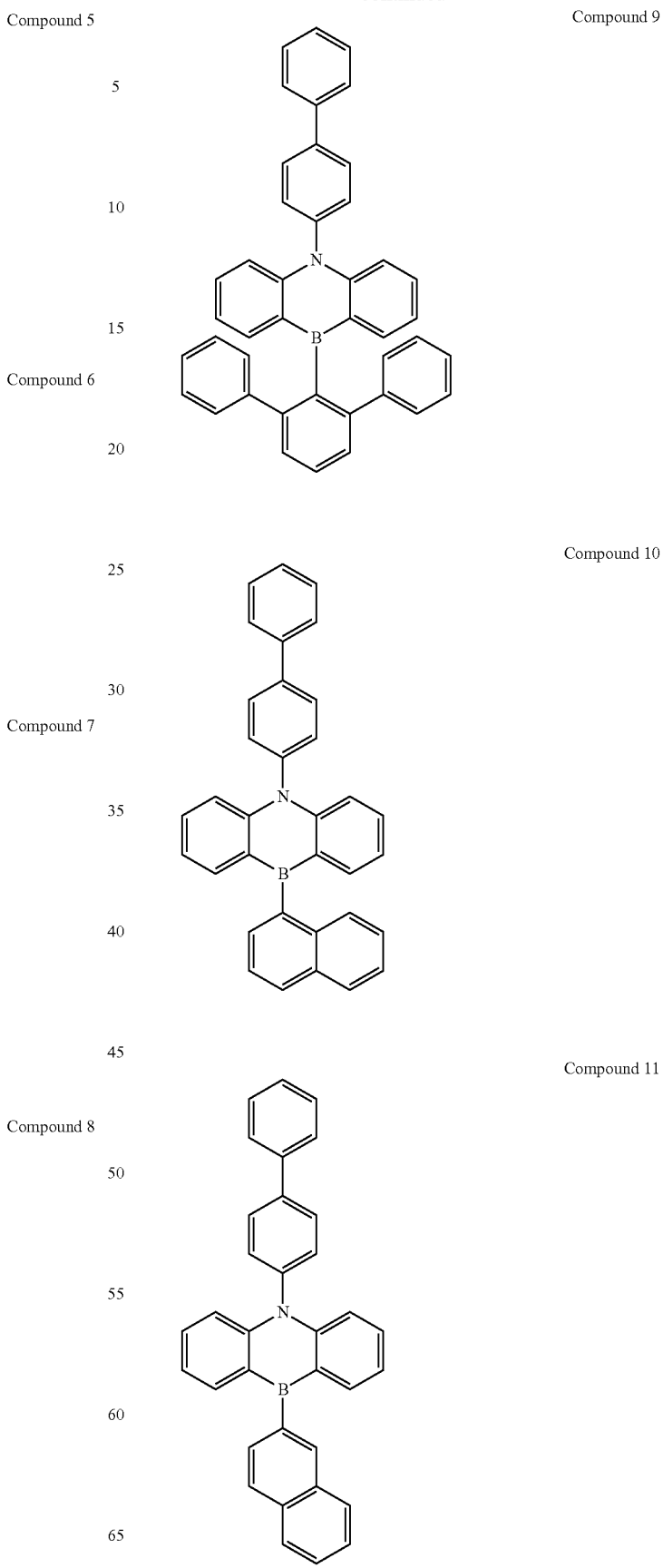
Compound 10
Compound 11

Compound 12
Compound 13
Compound 14
Compound 15
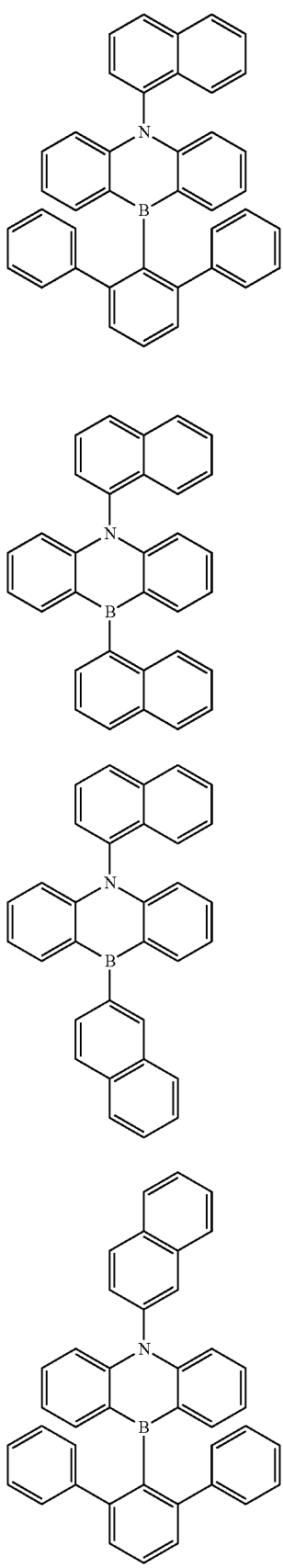
Compound 16
Compound 17
Compound 18
Compound 19
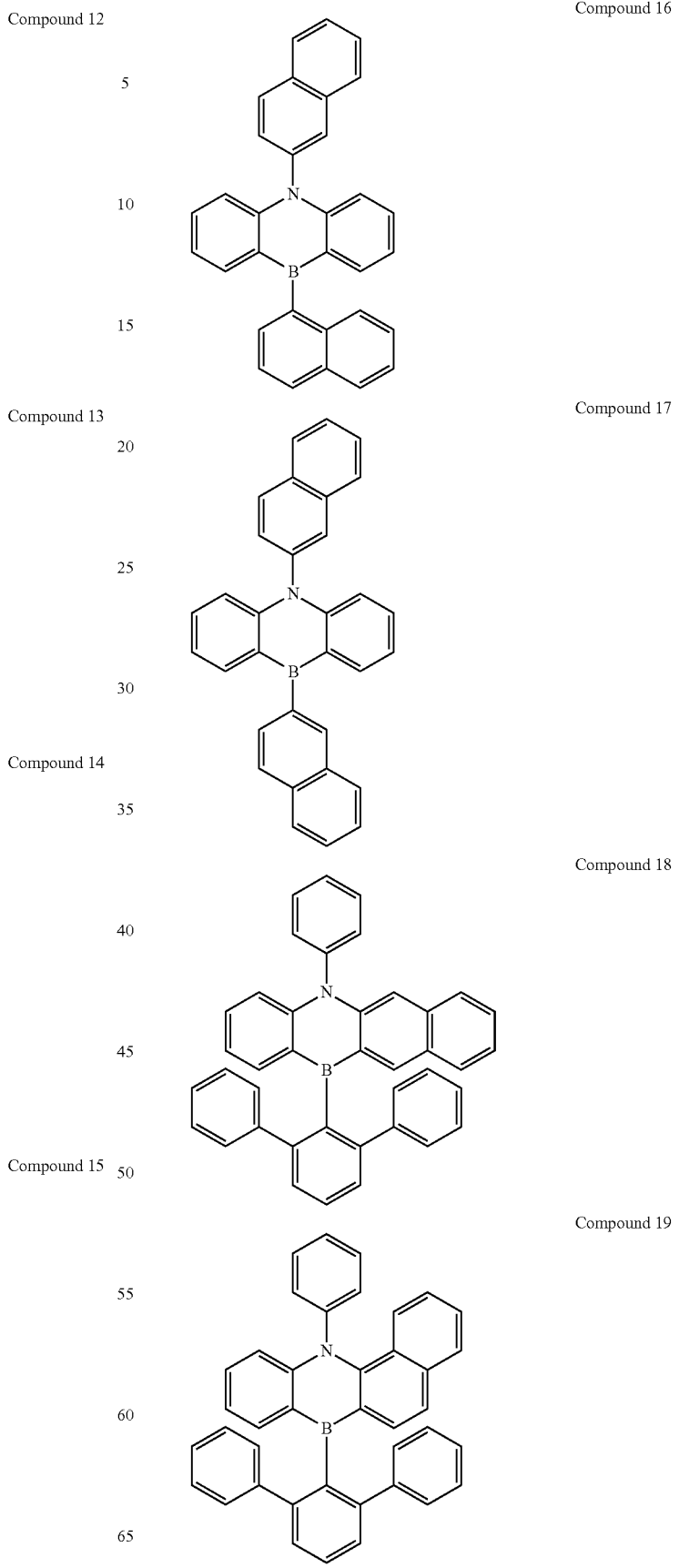

Compound 20
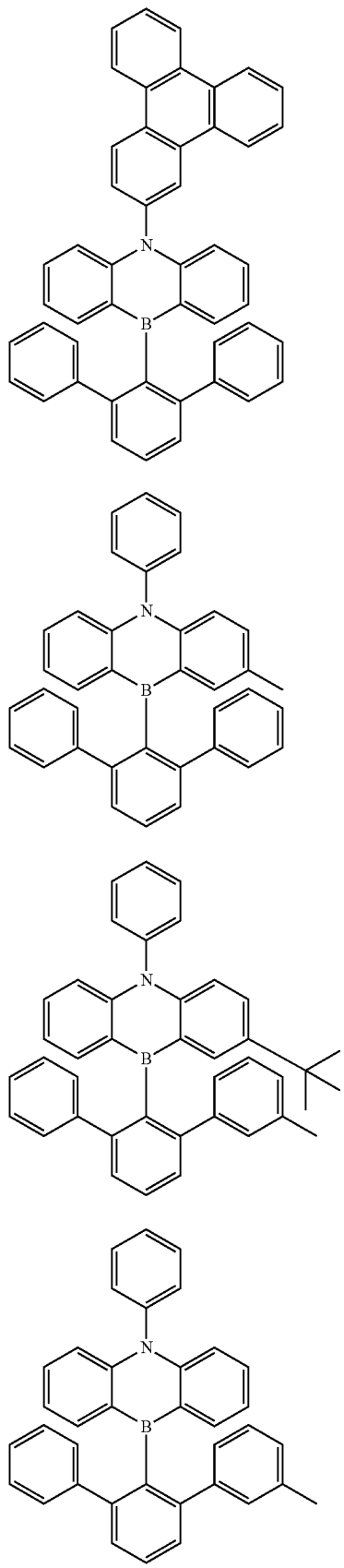
Compound 21
Compound 22
Compound 23
Compound 24
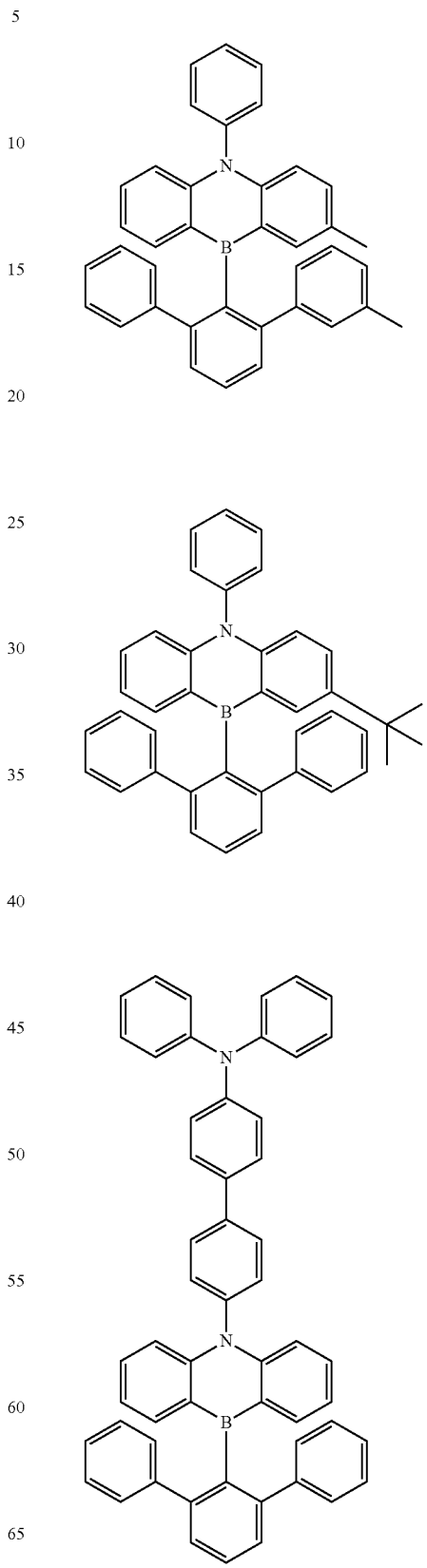
Compound 25
Compound 26

Compound 27
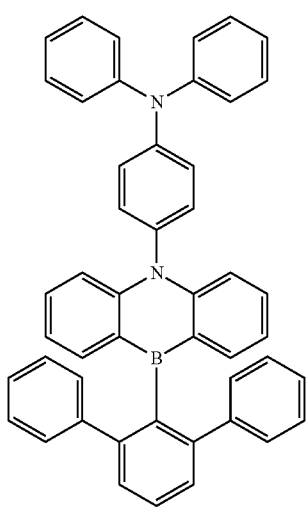
Compound 30
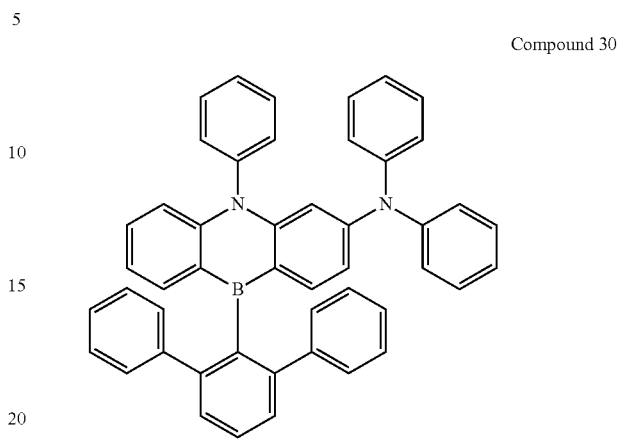
Compound 28
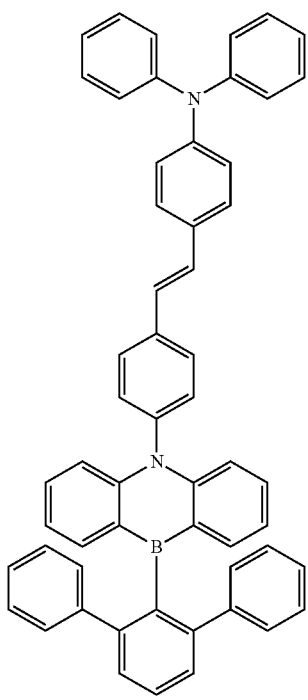
Compound 31
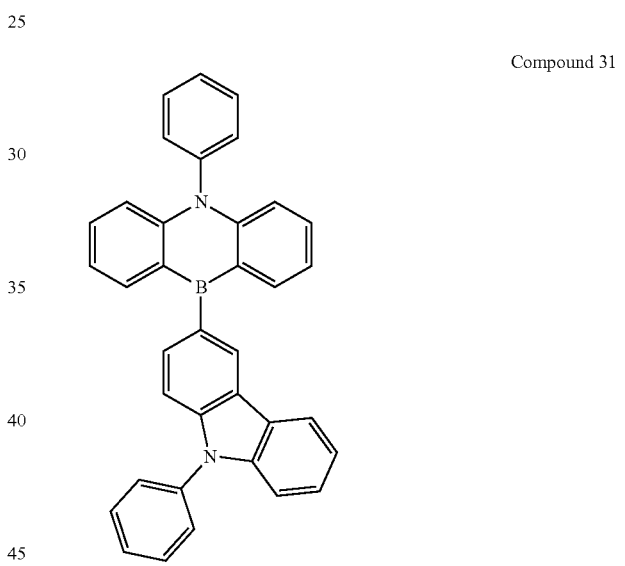
Compound 29
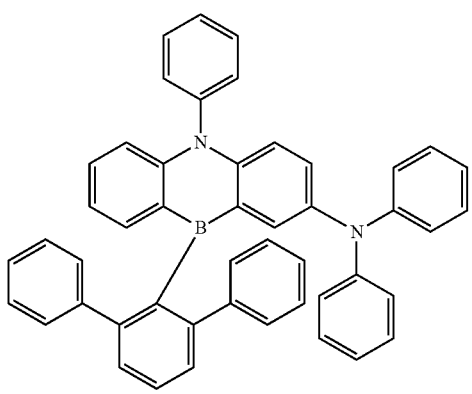
Compound 32
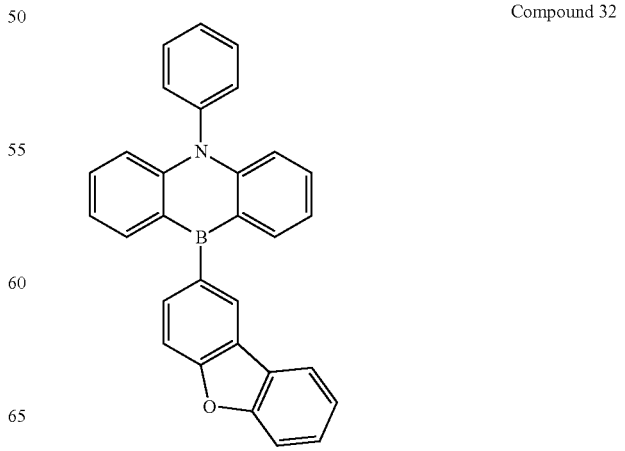

Compound 33
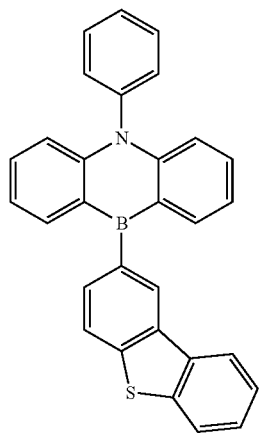
Compound 34
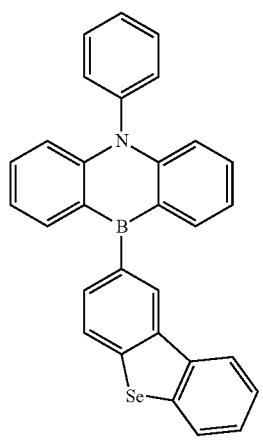
Compound 35
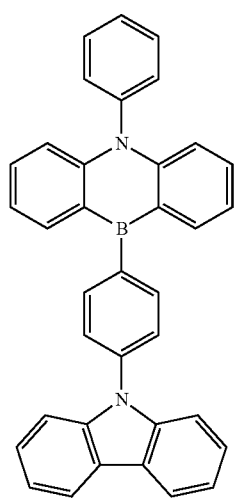
Compound 36
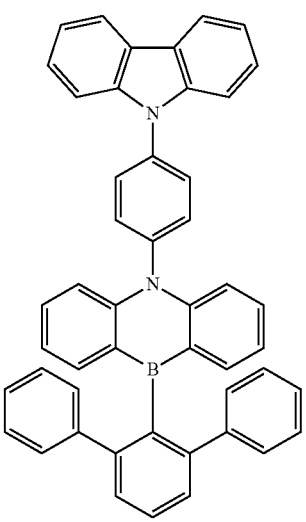
Compound 37
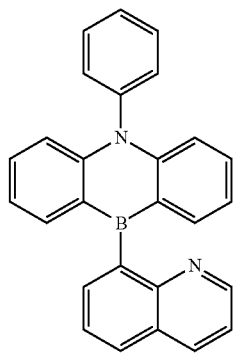
Compound 38
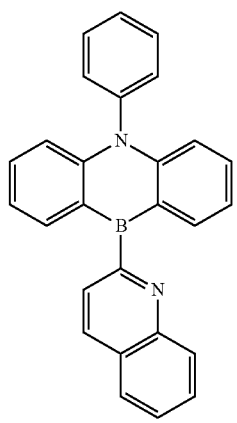

Compound 39
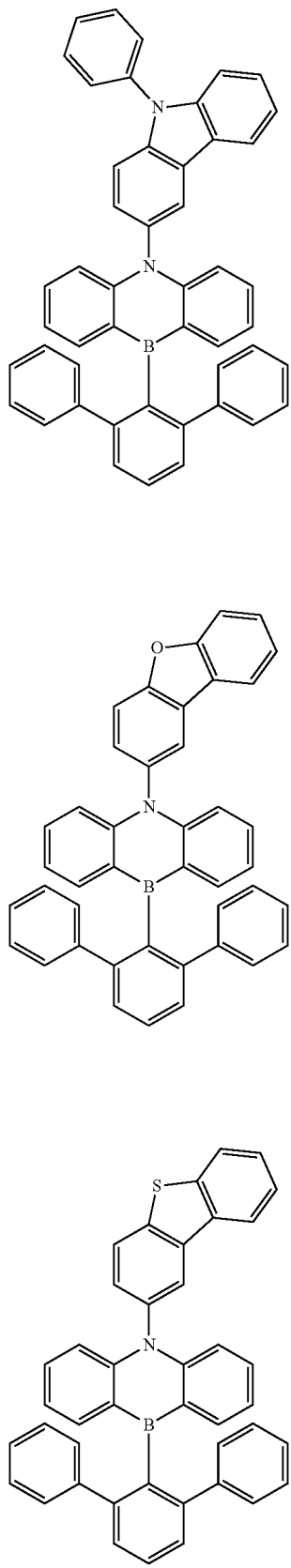
Compound 40
Compound 41
Compound 42
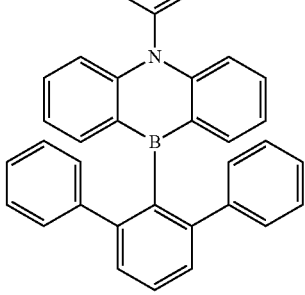
Compound 43
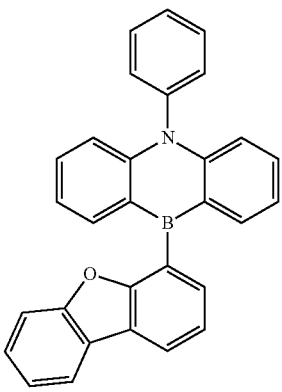
Compound 44
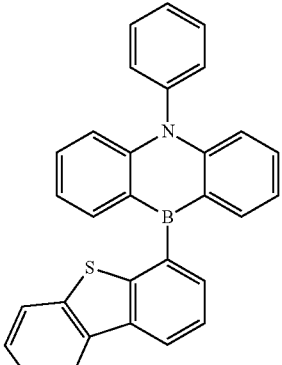
Compound 45
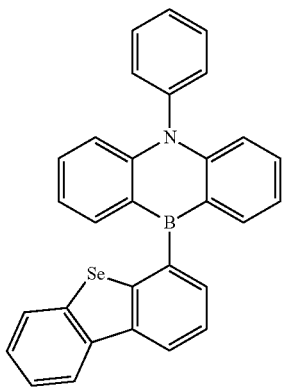

Compound 46
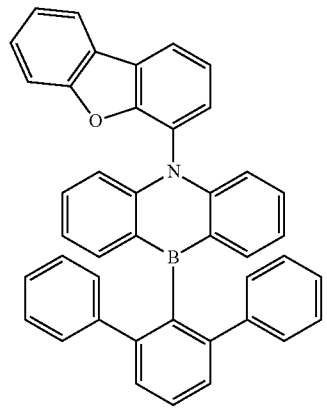
Compound 47
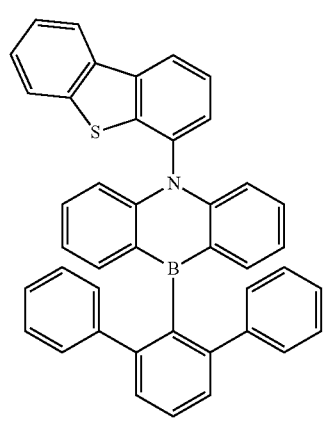
Compound 48
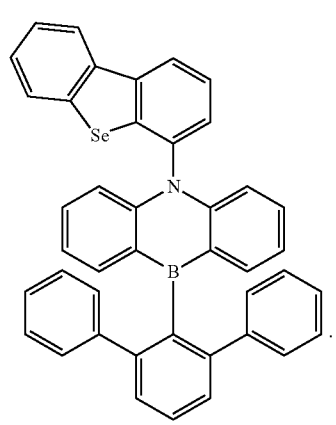
Compound 49
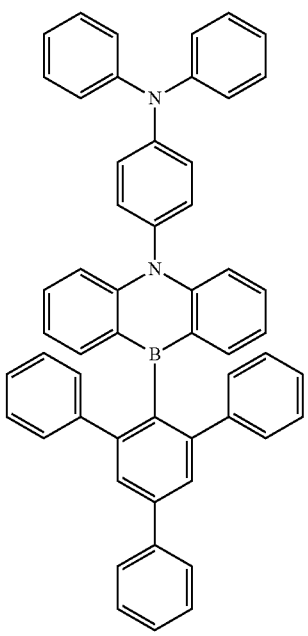
Compound 50
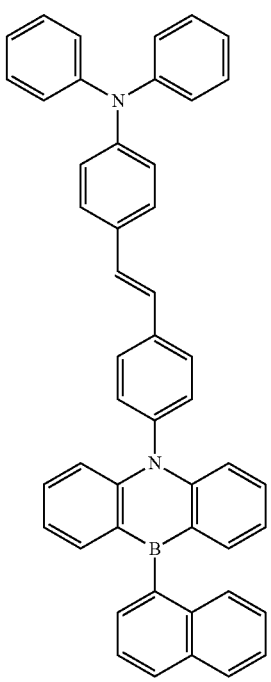
In another aspect, examples of azaborine compounds are provided and include compounds selected from the group consisting of:

51
-continued
Compound 51
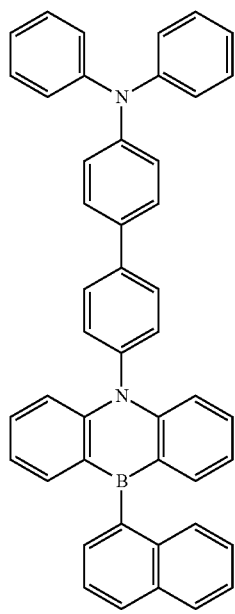
Compound 52
52
-continued
Compound 54
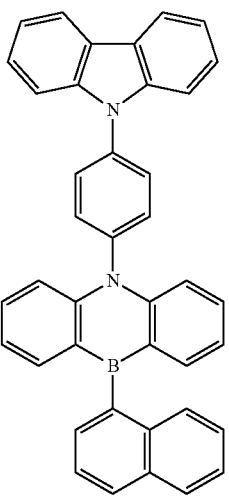
Compound 55
Compound 53
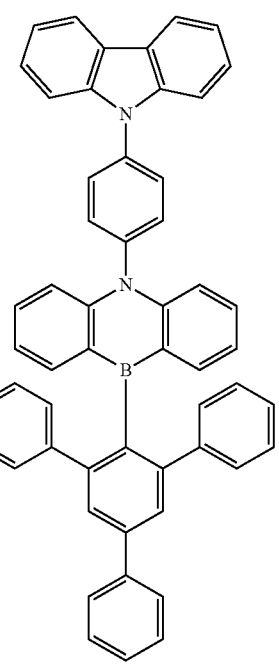

Compound 56
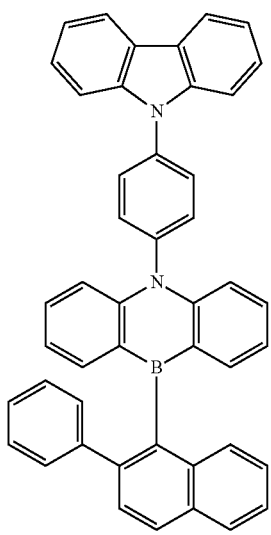
Compound 58
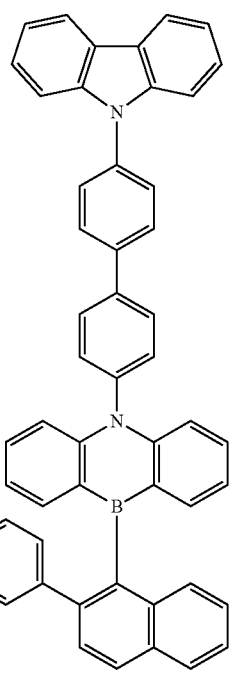
Compound 57
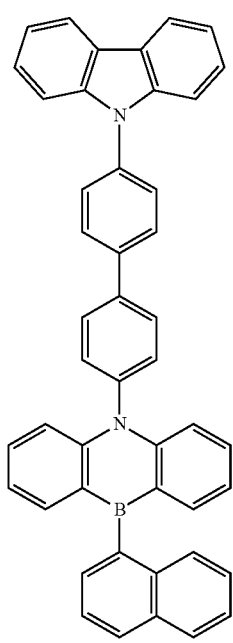
Compound 59
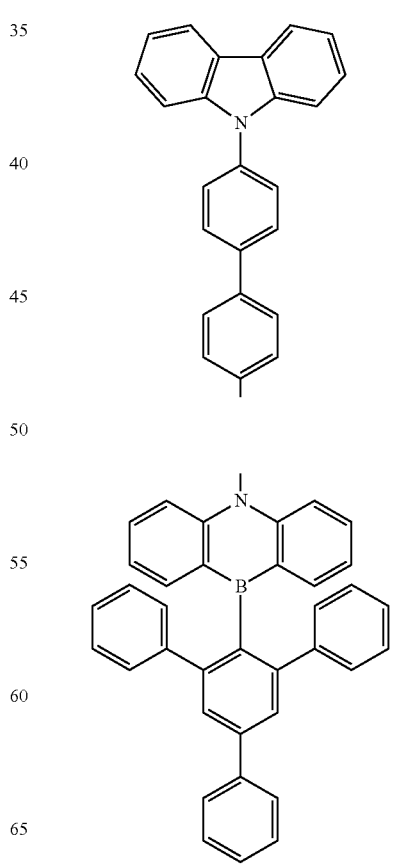

-continued

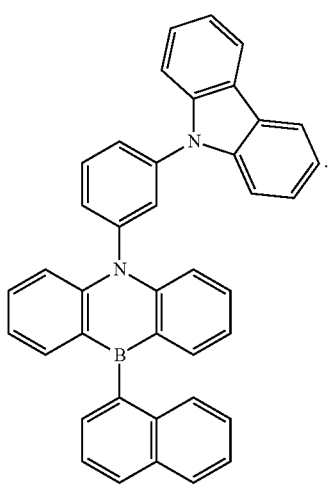

Compound 60

Additionally, a first device comprising an organic light-emitting device is provided. The organic light-emitting device comprises an anode, a cathode, and an organic layer, disposed between the anode and the cathode, and the organic layer further comprises a compound comprising the formula:

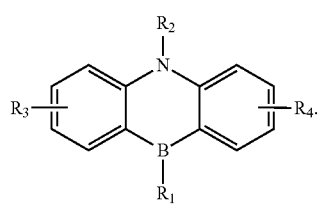

Formula I $R_1$ is a group containing two or more aryl or heteroaryl groups, and the aryl or heteroaryl groups are conjugated or fused. $R_3$ and $R_4$ may represent mono, di, tri, tetra, or penta substitutions. $R_2$, $R_3$ and $R_4$ are independently selected from hydrogen, alkyl, alkoxy, amino, alkenyl, alkynyl, aryl, and heteroaryl. Preferably, $R_2$ includes an aryl or a heteroaryl.

In one aspect, the compound comprises the formula:

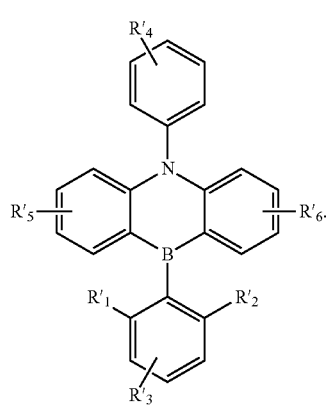

Formula II $R'_3$, $R'_4$, $R'_5$, and $R'_6$ may represent mono, di, tri, tetra, or penta substitutions. $R'_1$, $R'_2$, $R'_3$, $R'_4$, $R'_5$ and $R'_6$ are independently selected from hydrogen, alkyl, alkoxy, amino, alkenyl, alkynyl, aryl, and heteroaryl. At least one of $R'_1$ and $R'_2$ is an aryl or heteroaryl, and the aryl or heteroaryl groups are conjugated or fused.

In one aspect, $R'_3$, $R'_4$, $R'_5$, and $R'_6$ are independently aryl or heteroaryl.

In another aspect, $R'_4$ includes aryl or heteroaryl substitutions positioned ortho to the carbon atom in the aryl or heteroaryl group that is connected to the nitrogen atom.

Specific examples of azaborine compounds that may be used in the devices are provided, and include compounds selected from the group consisting of:

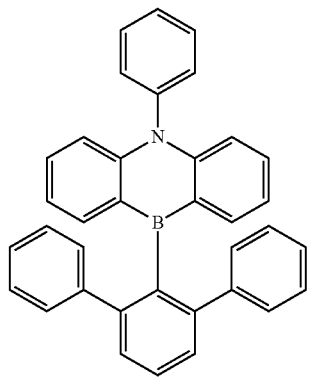

Compound 1

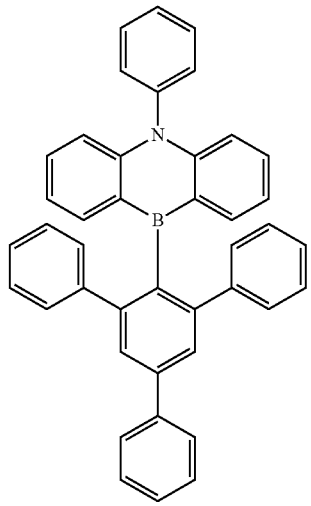

Compound 2

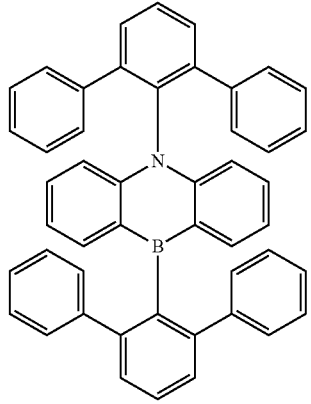

Compound 3

Compound 4
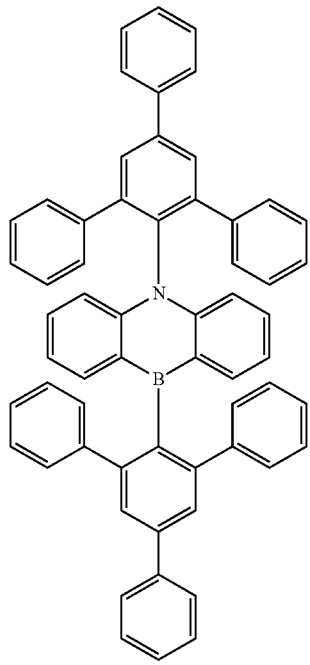
Compound 5
Compound 6
Compound 7
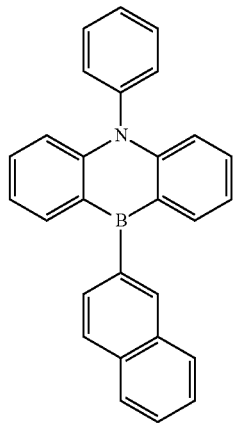
Compound 8
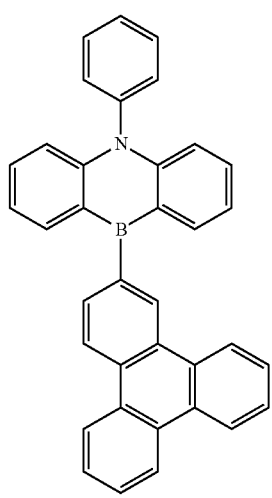
Compound 9
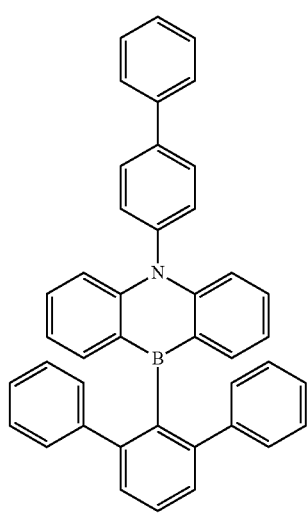

Compound 10
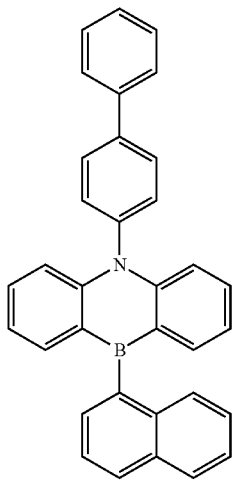
Compound 11
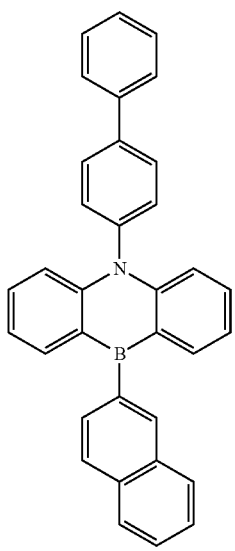
Compound 12
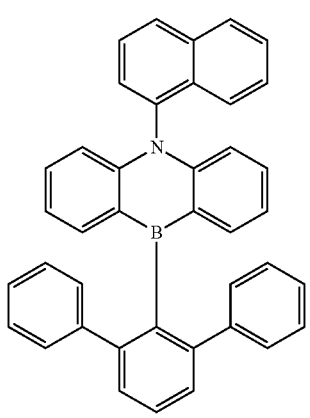
Compound 13
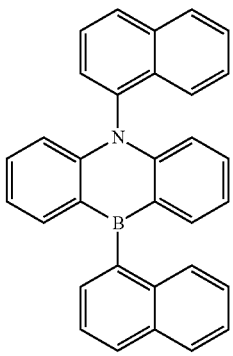
Compound 14
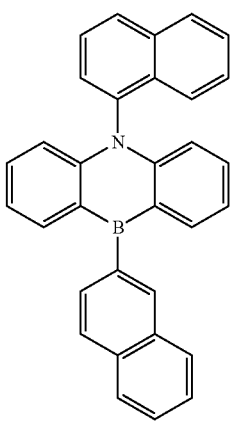
Compound 15
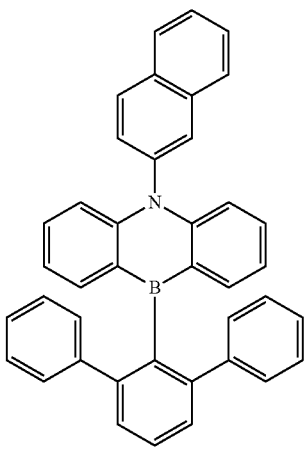
Compound 16
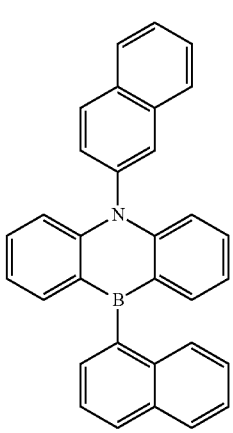

Compound 17
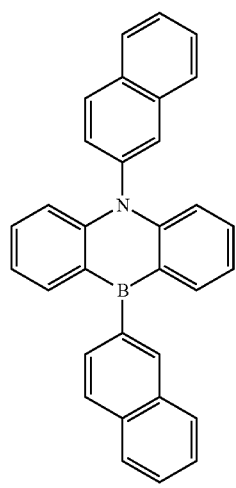
Compound 18
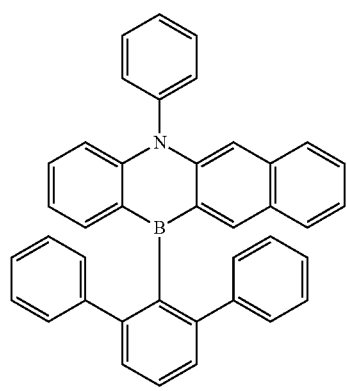
Compound 19
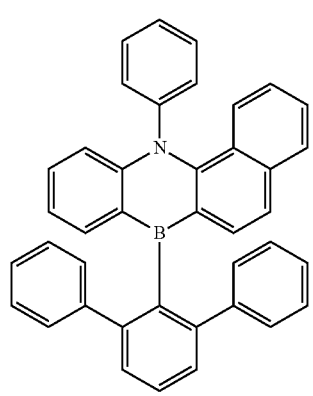
Compound 20
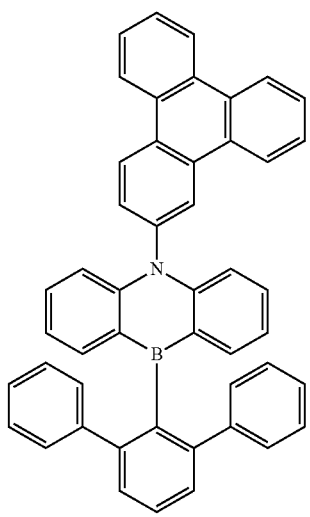
Compound 21
Compound 22
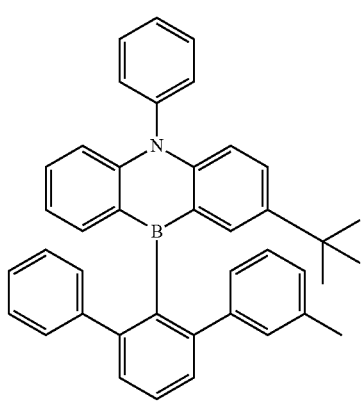

Compound 23
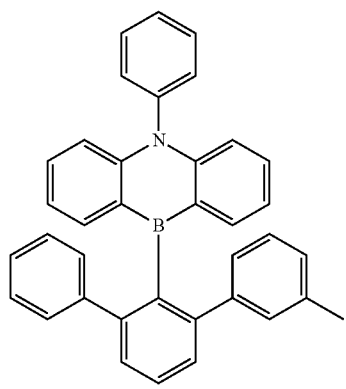
Compound 24
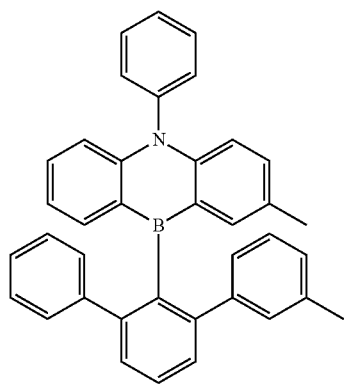
Compound 25
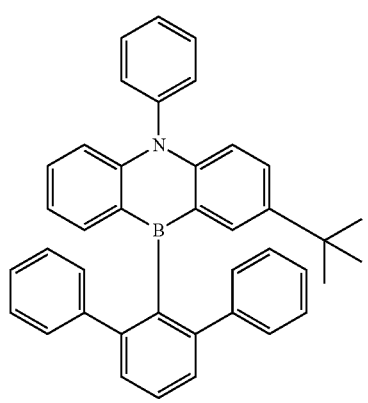
Compound 26
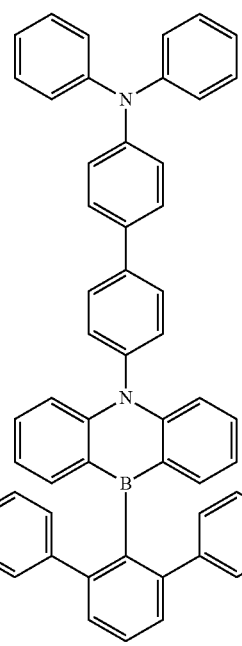
Compound 27
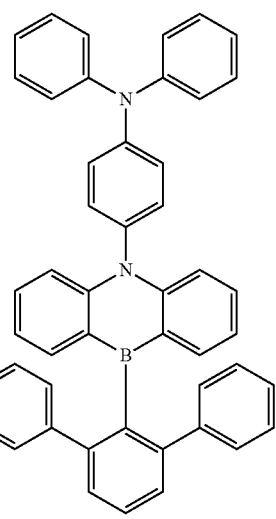

Compound 28
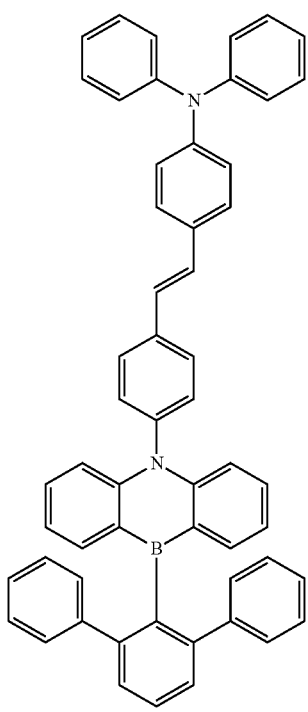
Compound 29
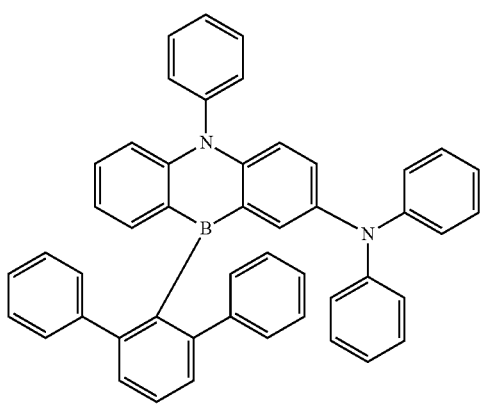
Compound 30
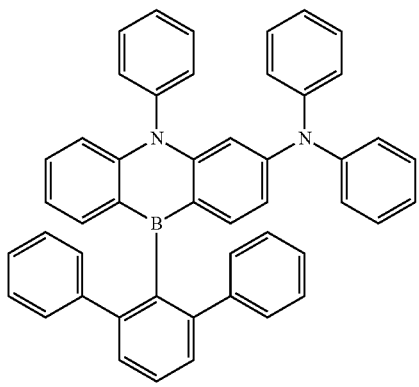
Compound 31
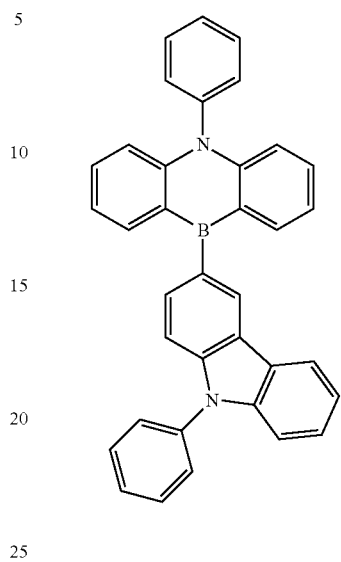
Compound 32
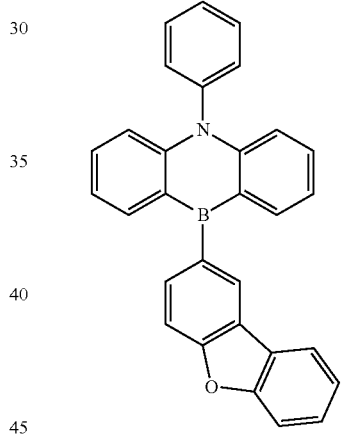
Compound 33
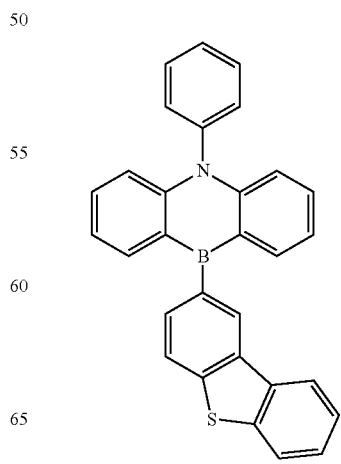

-continued
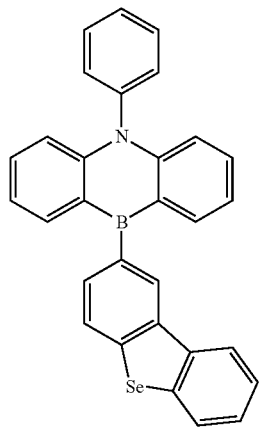
Compound 34
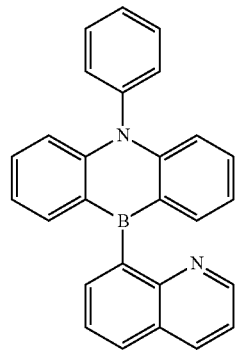
Compound 37
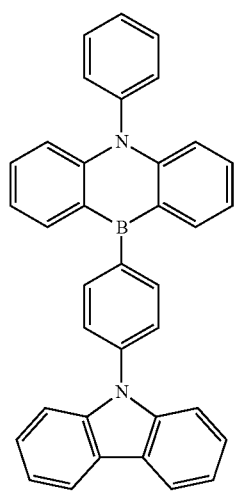
Compound 38
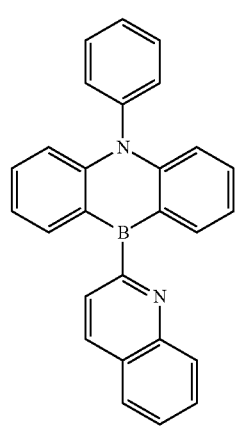
Compound 36
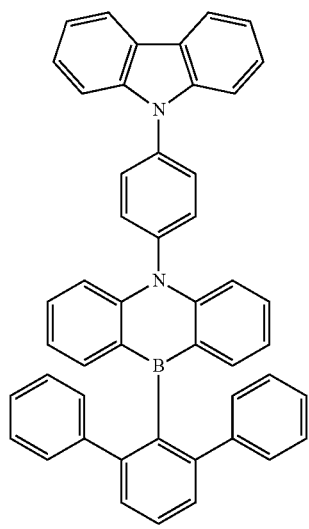
Compound 39
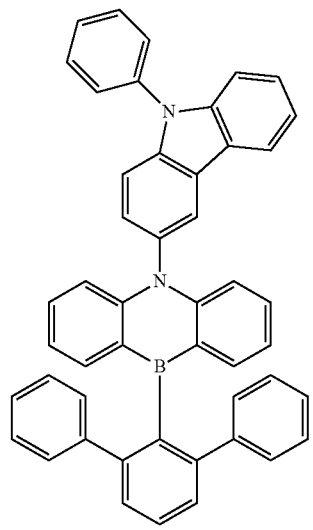

Compound 40
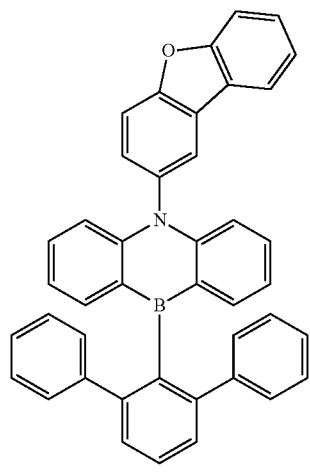
Compound 41
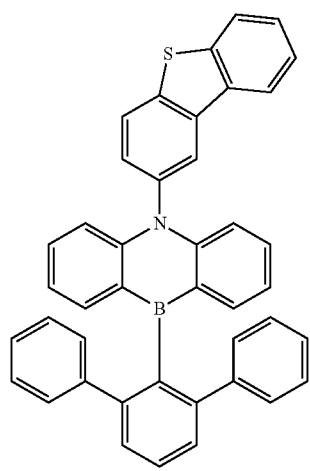
Compound 42
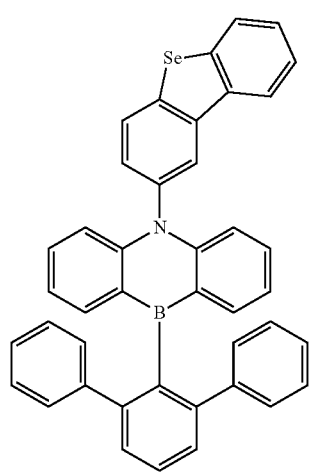
Compound 43
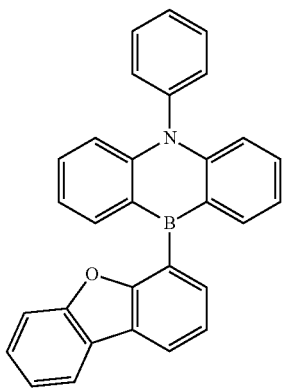
Compound 44
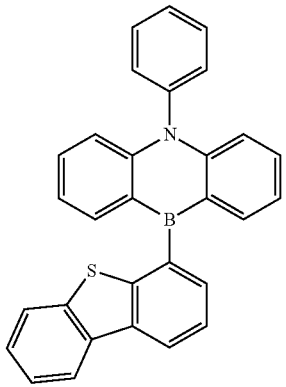
Compound 45
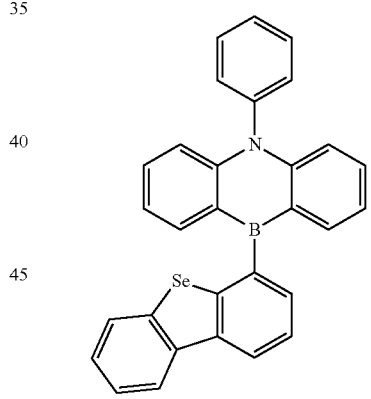
Compound 46
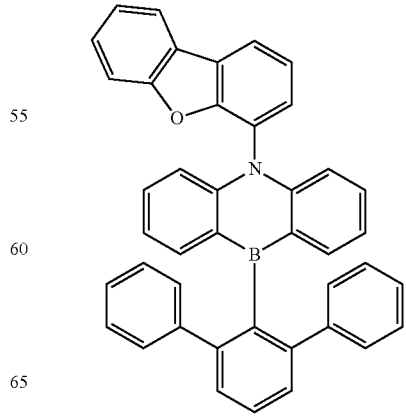

Compound 47
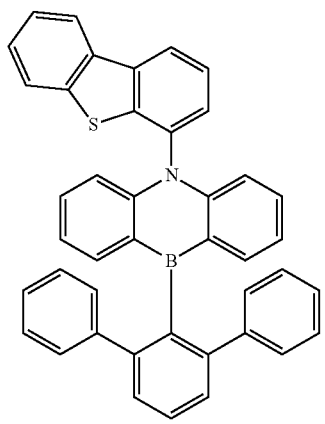
Compound 48
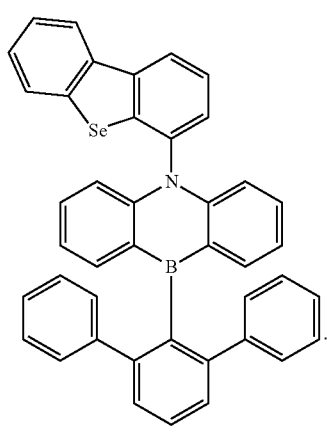
In another aspect, specific examples of azaborine compounds that may be used in the devices are provided, and include compounds selected from the group consisting of:
Compound 49
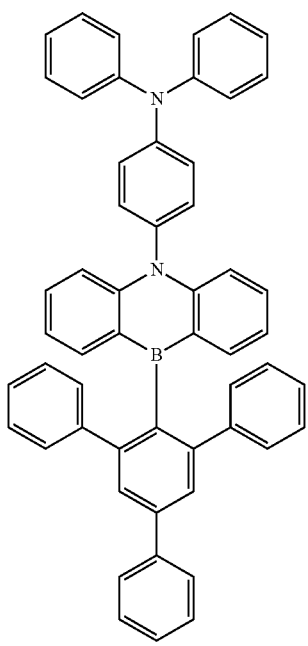
Compound 50
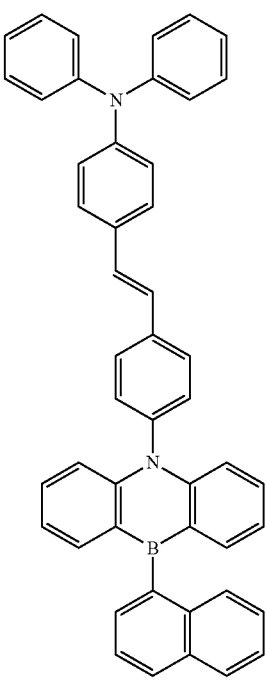
Compound 51
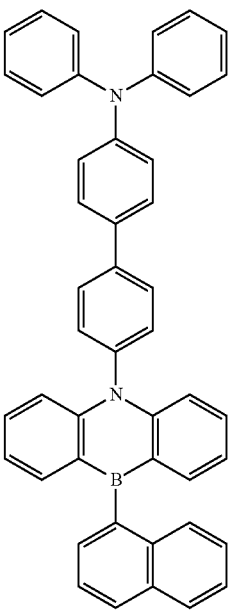

-continued
Compound 52
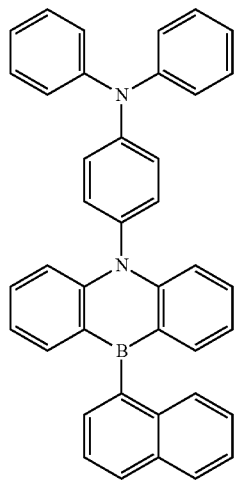
Compound 53
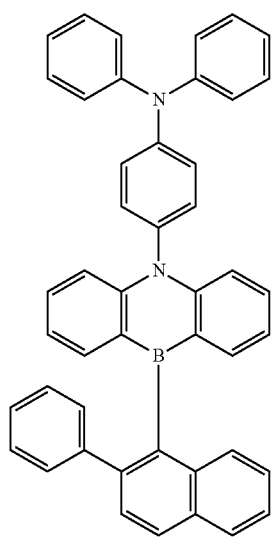
Compound 54
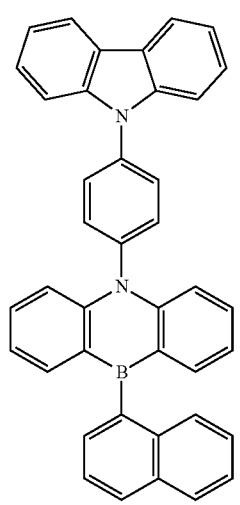
Compound 55
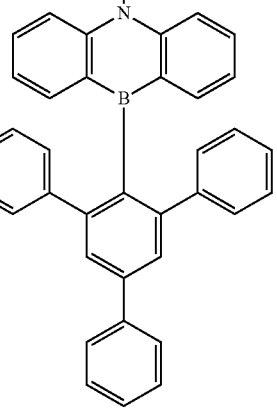
Compound 56
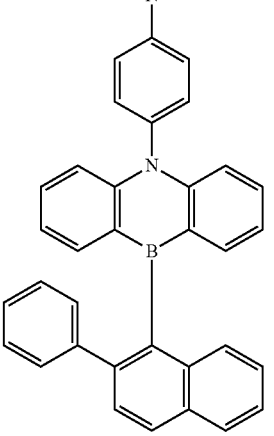

-continued

Compound 57

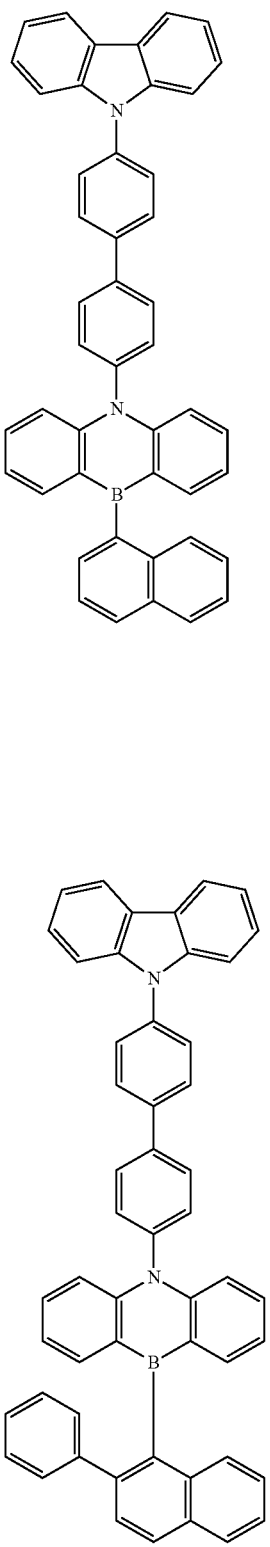

Compound 58

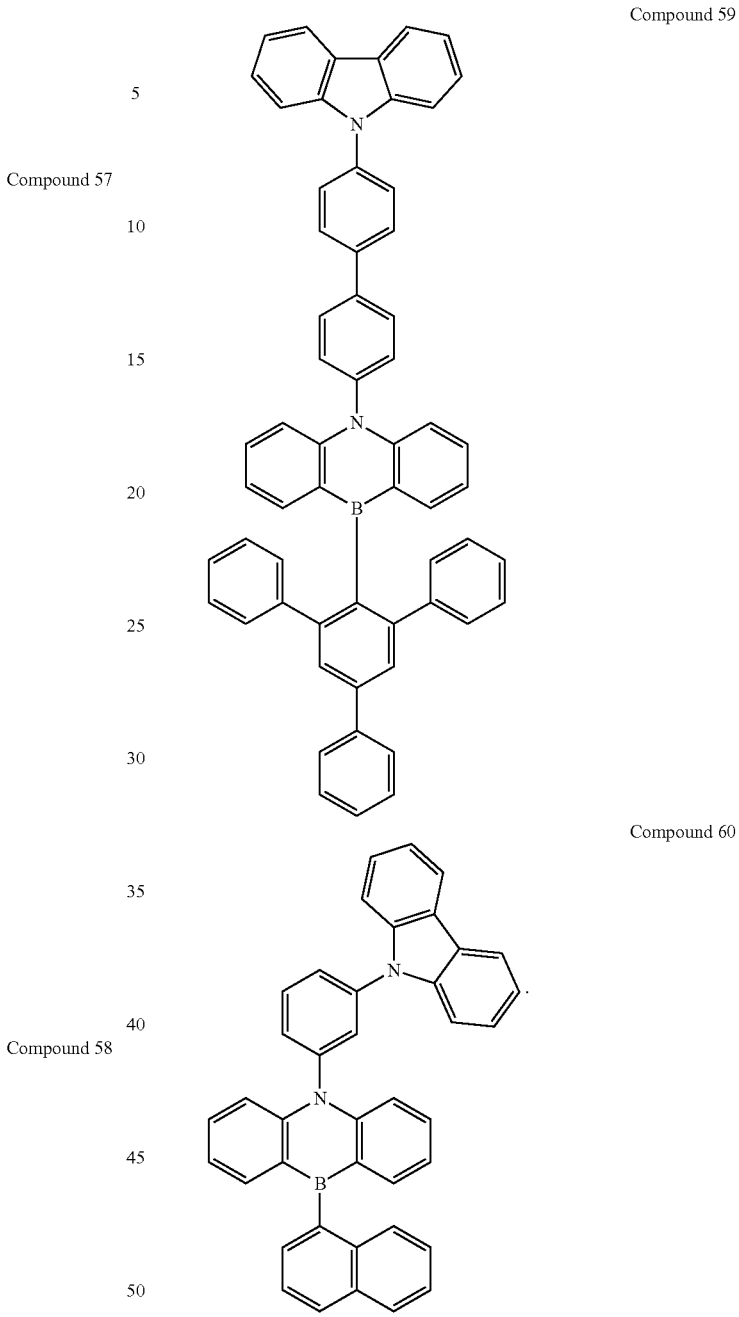

Compound 59

Compound 60

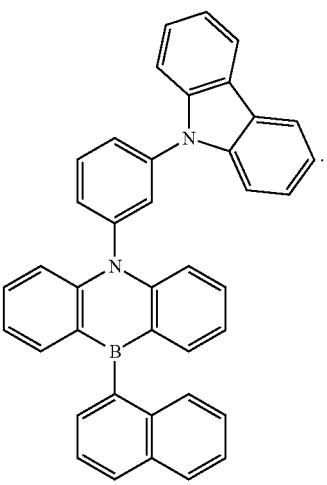

In one aspect, the organic layer is a blocking layer and the compound having Formula I is a blocking material.

In another aspect, the organic layer is an emissive layer and the compound comprising Formula I is a host. The organic layer may further comprise an emissive dopant. In yet another aspect, the organic layer is an emissive layer and the compound comprising Formula I is a fluorescent emitter.

In one aspect, the first device is a consumer product. In another aspect, the first device is an organic light-emitting device.

The materials described herein as useful for a particular layer in an organic light-emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

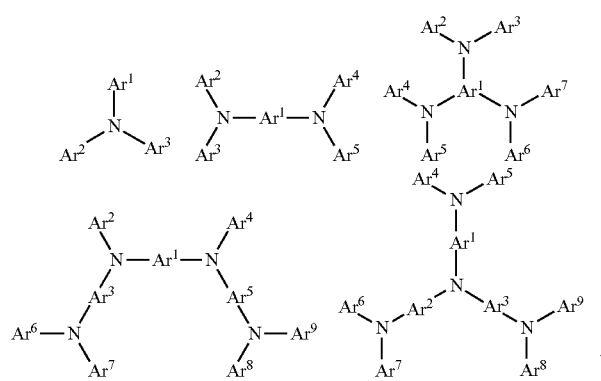

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, alkyl, alkoxy, amino, alkenyl, alkynyl, arylalkyl, heteroalkyl, aryl and heteroaryl.

In one aspect, $Ar^1$ to $Ar^9$ is independently selected from the group consisting of:

k is an integer from 1 to 20; $X^1$ to $X^8$ is CH or N; $Ar^1$ has the same group defined above.

Examples of metal complexes used in HIL or HTL include, but not limit to the following general formula:

M is a metal, having an atomic weight greater than 40; $(Y^1-Y^2)$ is a bidentate ligand, Y1 and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.

In another aspect, $(Y^1-Y^2)$ is a carbene ligand.

In another aspect, M is selected from Ir, Pt, Os, and Zn.

In a further aspect, the metal complex has a smallest oxidation potential in solution vs. Fc+/Fc couple less than about 0.6 V.

Host:

The light-emitting layer of the organic EL device of the present invention preferably contains at least a metal complex as light-emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

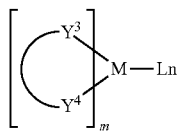

M is a metal; (Y³-Y⁴) is a bidentate ligand, Y³ and Y⁴ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

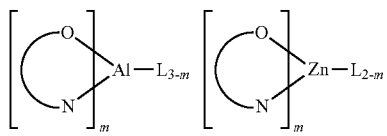

(O—N) is a bidentate ligand, having metal coordinated to atoms O and N.

In another aspect, M is selected from Ir and N.

In a further aspect, (Y³-Y⁴) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, triazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, alkyl, alkoxy, amino, alkenyl, alkynyl, arylalkyl, heteroalkyl, aryl and heteroaryl.

In one aspect, host compound contains at least one of the following groups in the molecule:

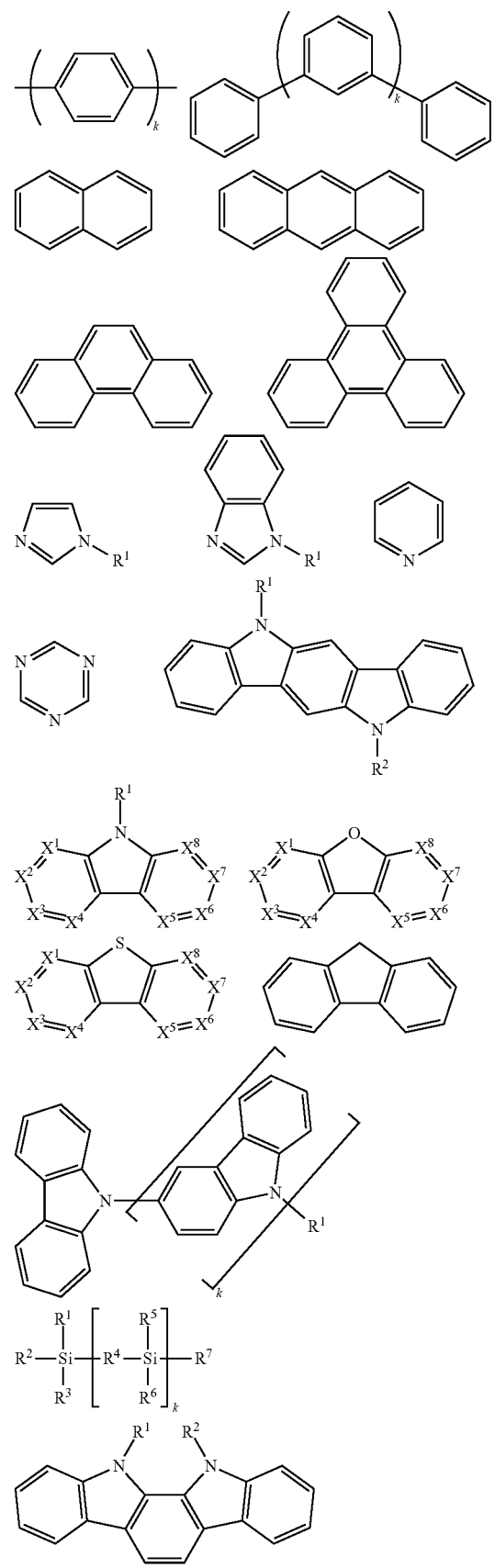

$R^1$ to $R^7$ is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

$X^1$ to $X^8$ is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

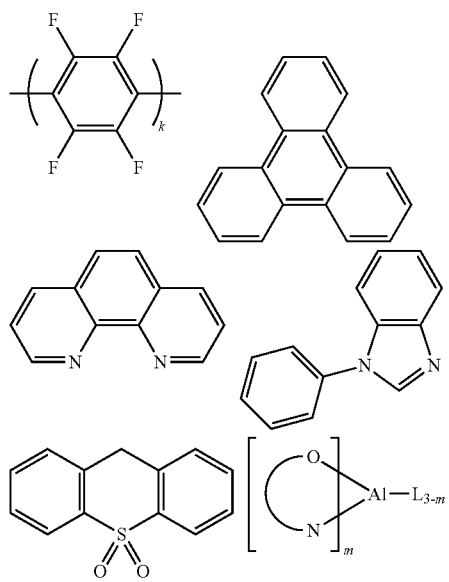

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

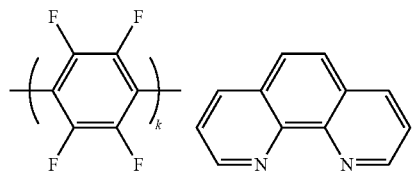

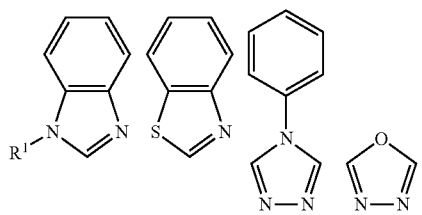

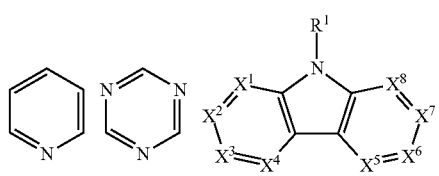

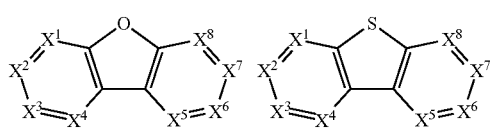

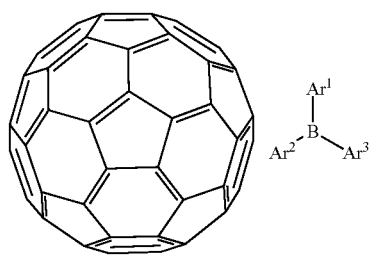

$R^1$ is selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above;

$Ar^1$ to $Ar^3$ has the similar definition as Ar's mentioned above;

k is an integer from 0 to 20;

$X^1$ to $X^8$ is selected from CH or N.

In another aspect, the metal complexes used in ETL contains, but not limit to the following general formula:

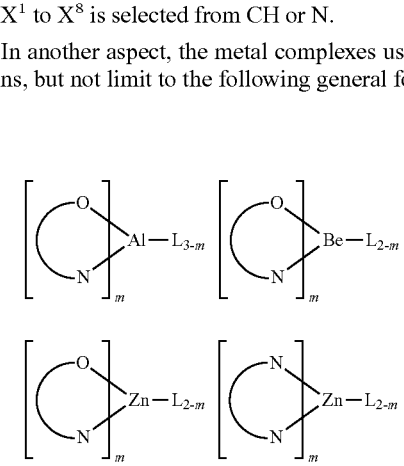

(O—N) or (N—N) is a bidentate ligand, having metal coordinated to atoms O, N or N, N; L is an ancillary ligand; m is an integer value from 1 to the maximum number of ligands that may be attached to the metal.

EXPERIMENTAL

Compound Examples

Example 1

Synthesis of Compound 2

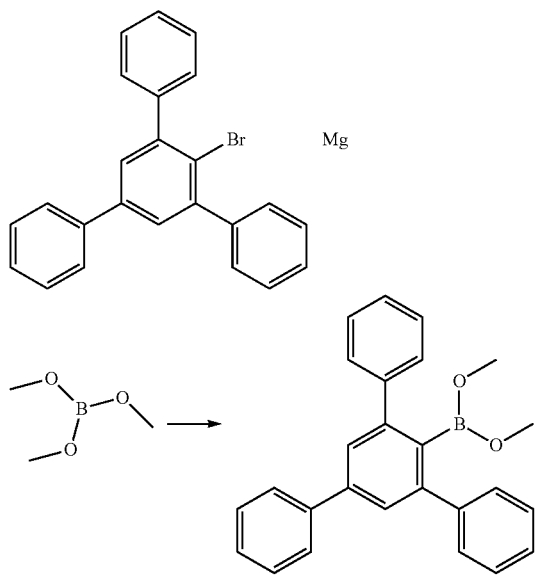

2'-bromo-5'-phenyl-1,1':3',1'-terphenyl was prepared according to the literature procedure (*Inorg. Chem.* 2003, 42, 6824). 2'-bromo-5'-phenyl-1,1':3',1'-terphenyl (10 g, 26 mmol) was dissolved in 10 mL of THF and refluxed with magnesium turnings (0.7 g, 28.5 mmol) for 16 h. The reaction mixture was cooled to 10° C., trimethylborate was added and the reaction heated to reflux for 16 h. Upon cooling, methanol and ethyl acetate were added and the reaction filtered through a plug of Celite. Upon removal of the solvent, 9 g (92%) of dimethyl (5'-phenyl-[1,1':3',1''-terphenyl]-2'-yl)boronate ester was isolated and used without further purification.

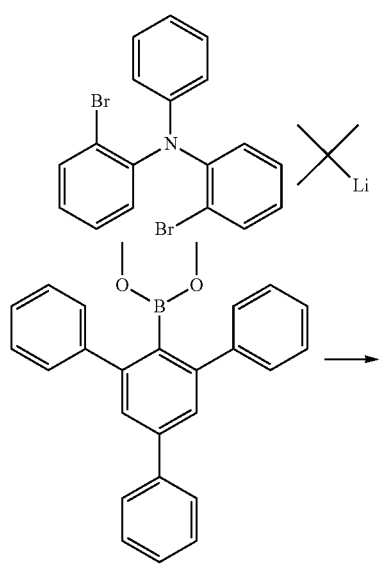

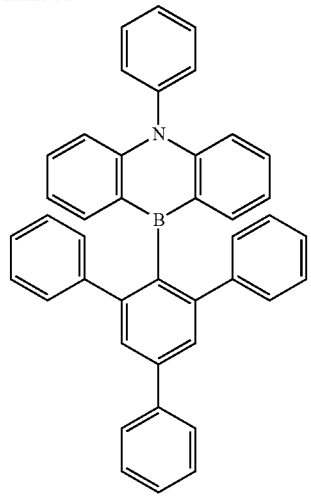

2-Bromo-N-(2-bromophenyl)-N-phenylaniline (1.0 g, 2.5 mmol) was dissolved in 50 mL of diethyl ether and the solution cooled to −78° C. tent-Butyllithium (10.9 ml, 1.7 molar solution pentane, 18.6 mmol) was added dropwise and the reaction mixture allowed to warm to 0° C. After stirring for 30 minutes at 0° C., the reaction mixture was then re-cooled to −78° C. Dimethyl (5'-phenyl-[1,1':3',1''-terphenyl]-2'-yl)boronate ester (1.2 g, 3.2 mmol) was dissolved in 10 mL of diethyl ether and added dropwise to reaction mixture. After warming to room temperature, the reaction was refluxed overnight, cooled and filtered through a plug of Celite with dichloromethane. The crude product was chromatographed on silica gel with 7(3 hexane/dichloromethane and further crystallized from hexane/dichlormethane to give 1.1 g (79%) of Compound 2.

Example 2

Synthesis of Compound X

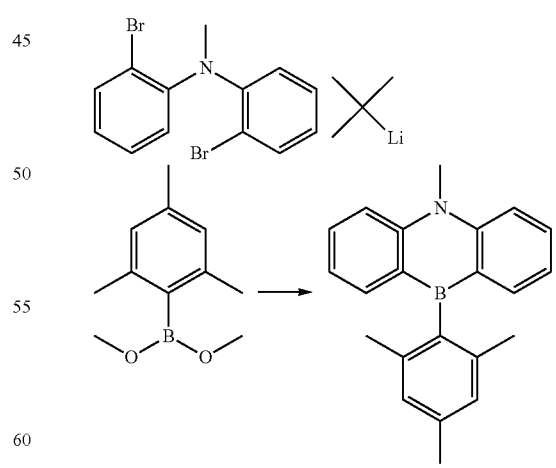

Compound X was prepared according to the literature procedure (*Org. Lett.* 2006, 8, 2241). 2-bromo-N-(2-bromophenyl)-N-methylaniline (0.5 g, 1.5 mmol) was dissolved in 50 mL of diethyl ether and the solution cooled to −78° C. tert-Butyllithium (4.3 mL of 1.7 molar solution in pentane, 7.3 mmol) was added dropwise and the reaction mixture allowed to warm to 0° C. and stirred for 30 minutes. Dimethylmesityldiboronate ester (0.37 g, 1.9 mmol) was dissolved in 10 mL of ether and added to reaction mixture dropwise. The reaction mixture was allowed to warm to room temperature, refluxed for 2 h, cooled, filtered through Celite with dichlormethane and concentrated. The crude product was chromatographed on silica gel with 9/1 hexane/ethyl acetate and further crystallized from hexane to give 0.13 g (55%) of the Compound X.

Example 3

Synthesis of Compound Y

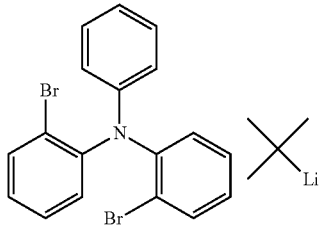

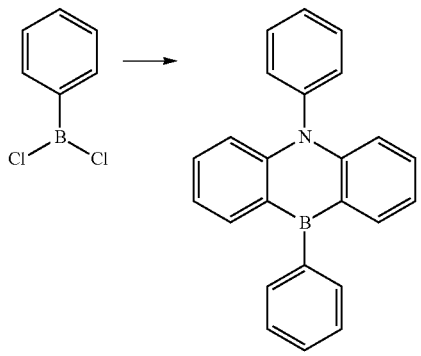

2-Bromo-N-(2-bromophenyl)-N-phenylaniline was prepared according to the literature procedure (*J. Org. Chem.* 1961, 2013). 2-Bromo-N-(2-bromophenyl)-N-phenylaniline (1.5 g, 3.7 mmol) was dissolved in 50 mL of diethyl ether and the solution cooled to −78° C. tert-Butyllithium (10.9 mL, 1.7 molar solution in pentane, 18.6 mmol) was added dropwise and the reaction mixture allowed to warm to 0° C. After stirring for 30 minutes at 0° C., the reaction mixture was then re-cooled to −78° C. Dichlorophenylborane (0.63 ml, 4.8 mmol) was dissolved in 10 mL of diethyl ether and added dropwise to reaction mixture. After warming to room temperature, the reaction was refluxed overnight, cooled and filtered through a plug of Celite with dichloromethane. The crude product was chromatographed on silica gel with 8/2 hexane/ethyl acetate and further crystallized from hexane to give 0.56 g (45%) of the Compound Y.

Example 4

Synthesis of Compound 49

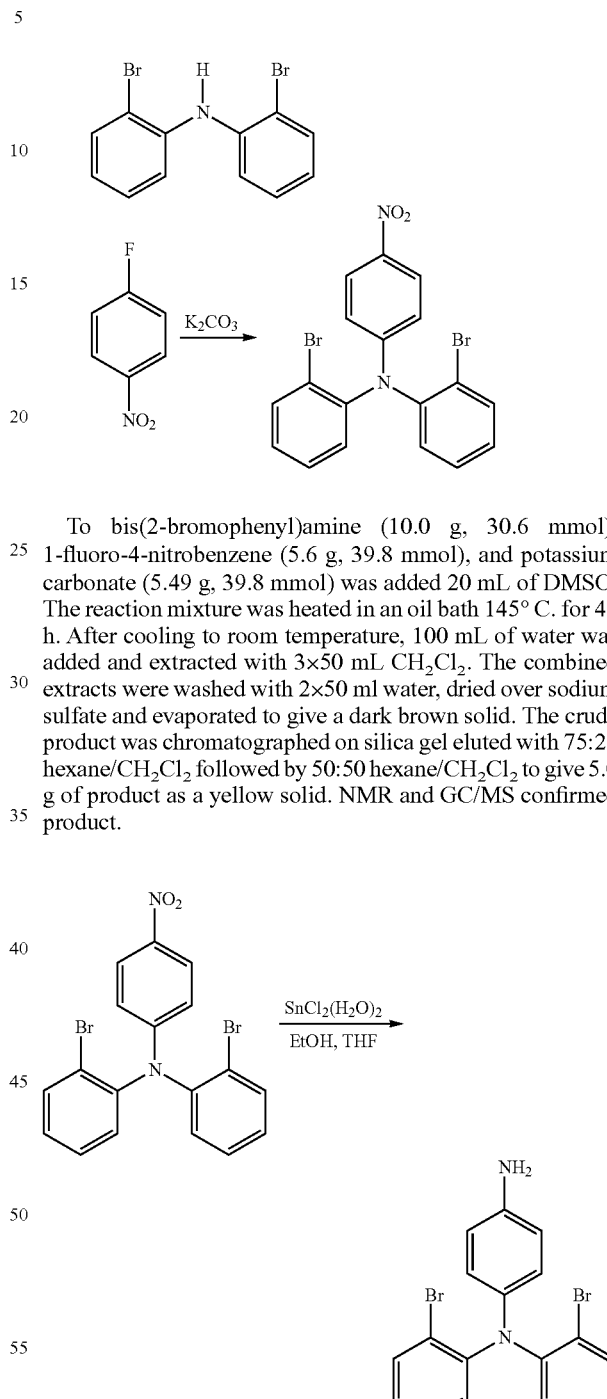

To bis(2-bromophenyl)amine (10.0 g, 30.6 mmol), 1-fluoro-4-nitrobenzene (5.6 g, 39.8 mmol), and potassium carbonate (5.49 g, 39.8 mmol) was added 20 mL of DMSO. The reaction mixture was heated in an oil bath 145° C. for 48 h. After cooling to room temperature, 100 mL of water was added and extracted with 3×50 mL $CH_2Cl_2$. The combined extracts were washed with 2×50 ml water, dried over sodium sulfate and evaporated to give a dark brown solid. The crude product was chromatographed on silica gel eluted with 75:25 hexane/$CH_2Cl_2$ followed by 50:50 hexane/$CH_2Cl_2$ to give 5.0 g of product as a yellow solid. NMR and GC/MS confirmed product.

2-Bromo-N-(2-bromophenyl)-N-(4-nitrophenyl)aniline (4.8 g, 10.71 mmol) and tin(II)chloride dihydrate (10.2 g, 53.6 mmol) were dissolved in ethanol (50 mL) and tetrahydrofuran (50 mL) and he solution heated to reflux. After 3 h, an additional 2.0 g tin(11) chloride was added and the reaction mixture heated for an additional 2 h at reflux. After cooling, the reaction was poured into 100 ml of ice and 50% aqueous sodium hydroxide solution was added until pH 14 was reached. The resulting caustic solution was extracted 3×75 mL with CH$_2$Cl$_2$. The combined organics were washed with 75 mL of water, dried over sodium sulfate and evaporated to give an orange solid. The crude product was chromatographed on silica gel eluted with 50:50 hexane/CH$_2$Cl$_2$ to give 3.8 g of product as a yellow solid. NMR confirmed product.

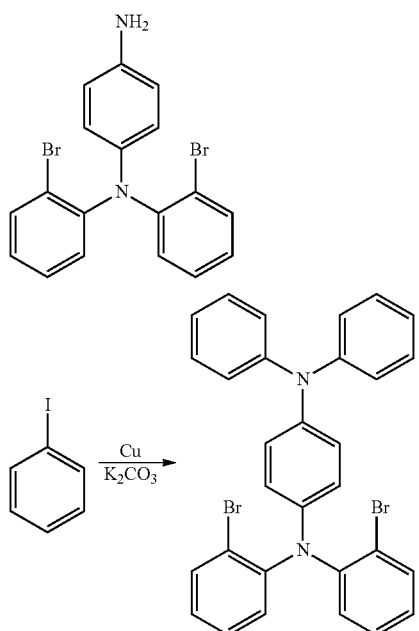

In a flask, N,N-bis(2-bromophenyl)benzene-1,4-diamine (0.5 g, 1.2 mmol), iodobenzene (2.44 g, 11.96 mmol), potassium carbonate (0.628 g, 4.54 mmol) and copper powder (0.038 g, 0.60 mmol) were combined and heated in an oil bath at 200° C. for 20 h. After cooling to room temperature, 25 ml of water was added and extracted with 3×15 mL CH$_2$Cl$_2$. The combined extracts were washed with 2×20 mL water, dried over sodium sulfate and evaporated leaving a dark brown liquid. The crude product was chromatographed on silica gel eluted with 90:10 hexane/CH$_2$Cl$_2$ followed by 75:25 hexane/CH$_2$Cl$_2$ to give 0.35 g of product as a white solid. NMR and GC/MS confirmed product.

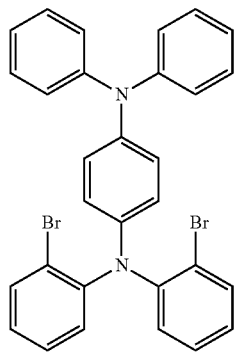

-continued

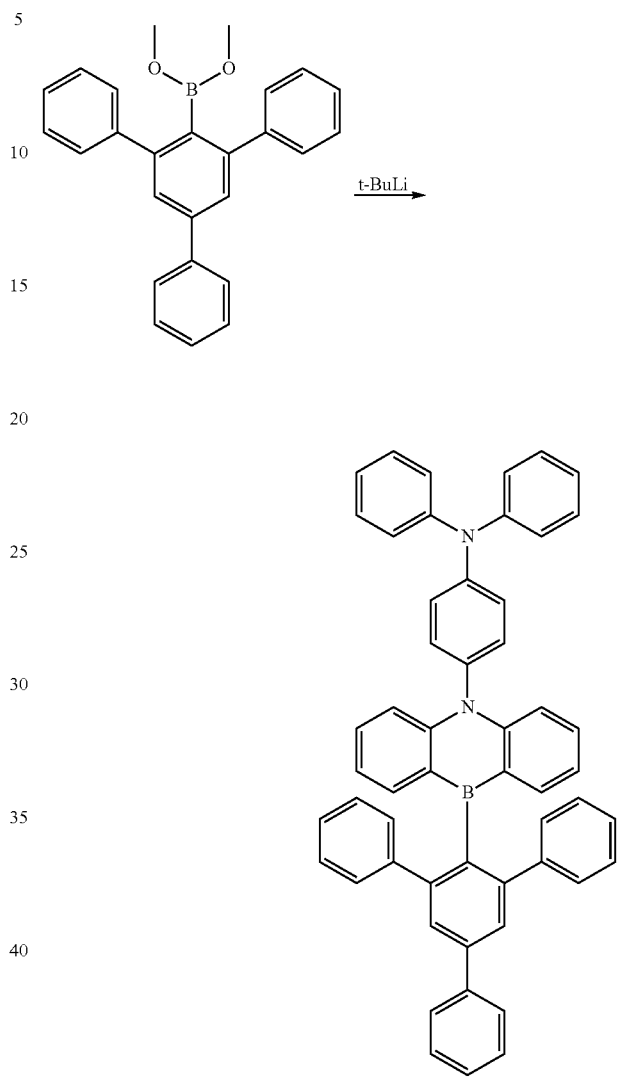

To a solution of N,N-bis(2-bromophenyl)-N',N'-diphenyl-benzene-1,4-diamine (1.5 g, 2.5 mmol) in ether (50 ml) at −78° C. was added tert-butyllithium (7.5 mL, 1.7 M in pentane, 12.7 mmol) dropwise. The reaction was warmed to 0° C. for 30 minutes before being recooled to −78° C. A solution of dimethyl(5'-phenyl-[1,1',3',1''-terphenyl]-4'-yl)boronate (1.3 g, 3.4 mmol) in 25 ml of ether was added dropwise, the bath was removed and the reaction mixture allowed to warm to room temperature, after which it was heated at reflux overnight. After cooling to room temperature, hexane and EtOAc were added and the mixture filtered through celite and the filtrate was evaporated to give a yellow solid. The crude product was chromatographed on silica gel eluted with 98:2 hexane/CH$_2$Cl$_2$ to give 0.5 g of Compound 49. NMR and MS confirmed product.

Example 5

Synthesis of Compound 53

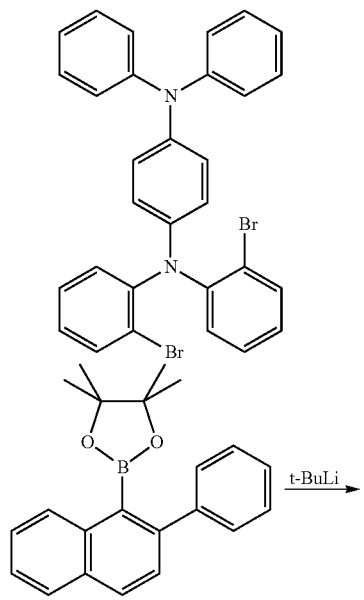

4,4,5,5-Tetramethyl-2-(2-phenylnaphthalen-1-yl) [1,3,2]-dioxaborolane was prepared according to the procedure of Spivey et al., *J. Org. Chem.* 2003, 68, 7379. To a solution of N,N-bis(2-bromophenyl)-N4,N4-diphenylbenzene-1,4-diamine (0.5 g, 0.88 mmol) in 25 ml ether, cooled in a dry ice/acetone bath to −78° C., was added tert-butyllithium (2.6 mL, 4.4 mmol, 1.7 M in pentane) dropwise. The ice bath was removed and the reaction mixture was allowed to warm to 0° C. and stirred for 30 min. The reaction mixture was recooled to −78° C. and a solution of 4,4,5,5-tetramethyl-2-(2-phenyl-naphthalen-1-yl)[1,3,2]-dioxaborolane (0.38 g, 1.14 mmol) in 10 mL of ether was added dropwise. After stirring for 30 min. at −78° C., the bath was removed and the solution allowed to warm to room temperature and subsequently heated to reflux overnight. After cooling, the reaction was quenched by adding 2 ml MeOH and filtered through celite, washing with CH$_2$Cl$_2$. After evaporation of the solid, the crude product was chromatographed on silica with 90:10 hexane:CH$_2$Cl$_2$ followed by 75:25 hexane:CH$_2$Cl$_2$ to give 0.15 g of Compound 53. NMR and LC/MS confirmed product.

Device Examples

All device examples were fabricated by high vacuum (<10$^{-7}$ Torr) thermal evaporation. The anode electrode is indium tin oxide (ITO). The cathode consisted of 10 Å of LiF followed by 1,000 Å of Al. All devices were encapsulated with a glass lid sealed with an epoxy resin in a nitrogen glove box (<1 ppm of H$_2$O and O$_2$), and a moisture getter was incorporated inside the package.

The organic stack of the Device Example 1 in Table 2 consists of sequentially, from the ITO surface, 100 Å of E1 as the hole injection layer (HIL), 300 Å of NPD as the hole transporting layer (HTL), 300 Å of Compound 2 doped with 15 wt % of Compound A as the emissive layer (EML), 50 Å of Compound 2 as the ETL2 and 400 Å of BAlq as the ETL1. Compound 2 evaporated at ~230° C. at ~10$^{-8}$ Torr.

Comparative Device Example 1 is similar to the Device Example 1 except the EML is Compound B doped with 10 wt % of E1 and the ETL2 is Compound C.

As used herein, the following compound have the following structures:

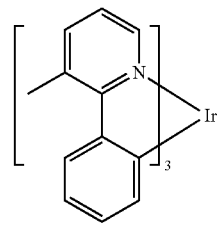

E1

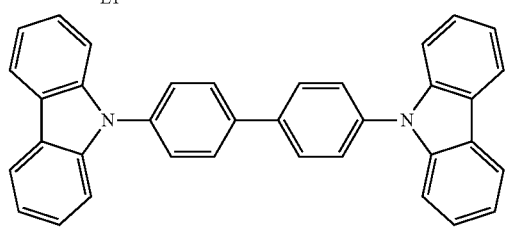

CBP

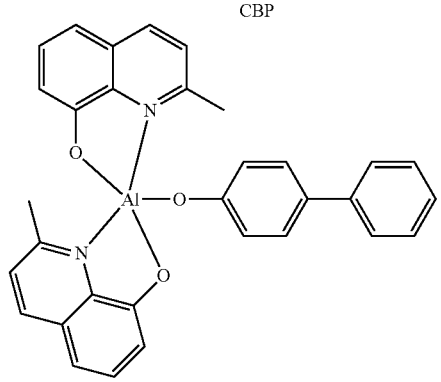

BAlq

Particular materials for use in an OLED are provided. In particular, the materials may be used as host materials and/or emitting dopant in the emissive layer of such a device. The materials may also be used in non-emissive layers, such as the blocking layer. The compounds provided herein may improve device lifetime.

TABLE 2

| Device Example | Host | % E1 | ETL2 | 1931 CIE x | 1931 CIE y | At 1000 cd/m² V [V] | At 1000 cd/m² LE [cd/A] | At 1000 cd/m² EQE [%] | At 1000 cd/m² PE [lm/W] |
|---|---|---|---|---|---|---|---|---|---|
| 1 | Compound 2 | 15 | Compound 2 | 0.3202 | 0.6263 | 5.7 | 32.9 | 9.2 | 18.0 |
| Comparative 1 | CBP | 10 | BAlq | 0.346 | 0.614 | 7.0 | 33.4 | 9.2 | 15.0 |

From Table 2, it can be seen that the efficiency of the device using Compound B as the host with Compound A, an Ir(ppy)$_3$-type compound, as the dopant, is comparable to a standard device using CBP as the host.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound comprising the formula:

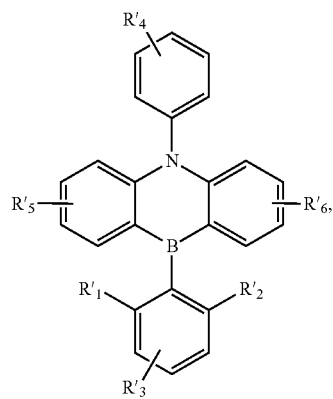

Formula II wherein R'$_4$, may represent mono, di, tri, or tetra substitutions;

wherein R'$_5$ and R'$_6$, may represent mono, di, tri, tetra, substitution;

wherein R'$_3$, may represent mono, di, or tri substitutions;

wherein R'$_1$ and R'$_2$, are independently selected from aryl and heteroaryl, wherein R'$_3$, R'$_4$, R'$_5$, and R'$_6$ are independently selected from hydrogen, alkyl, alkoxy, amino, alkenyl, alkynyl, aryl, and heteroaryl; and wherein the aryl or heteroaryl groups are conjugated or fused.

2. The compound of claim 1, wherein R'$_3$, R'$_4$, R'$_5$, and R'$_6$ are independently aryl or heteroaryl.

3. The compound of claim 1, wherein R'$_4$ includes aryl or heteroaryl substitutions positioned ortho to the carbon atom in the phenyl group that is connected to the nitrogen atom.

4. A compound selected from the group consisting of:

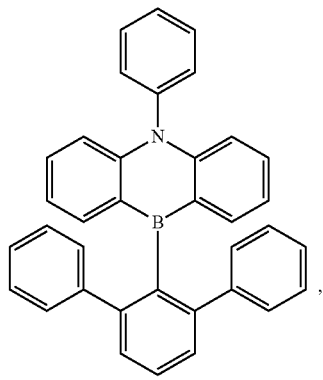

Compound 1

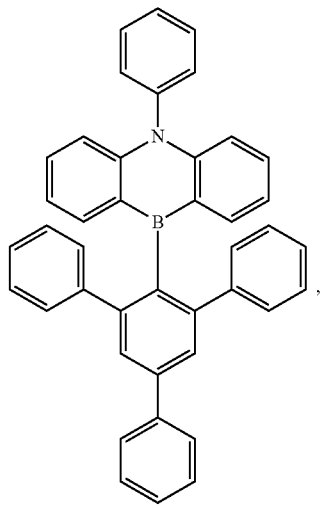

Compound 2

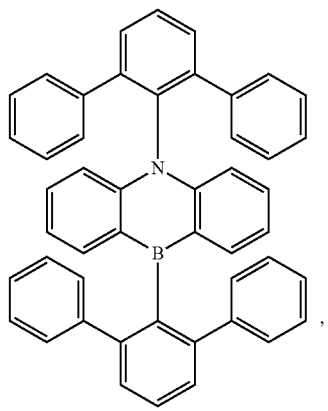

Compound 3

Compound 4
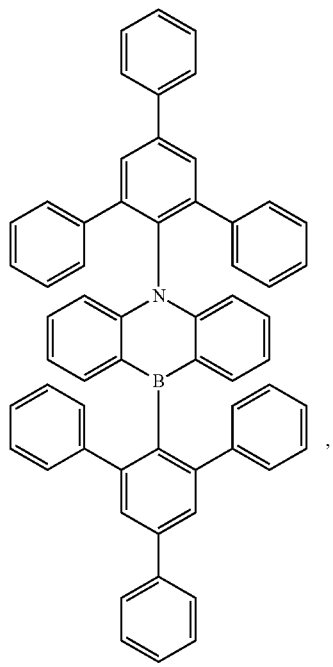
Compound 9
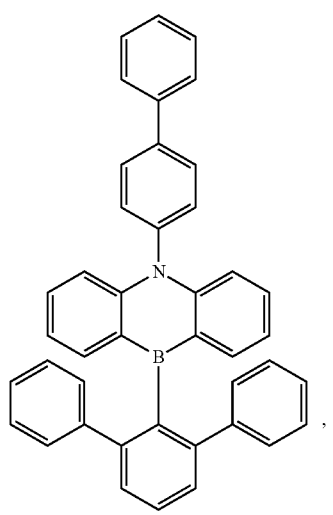
Compound 12
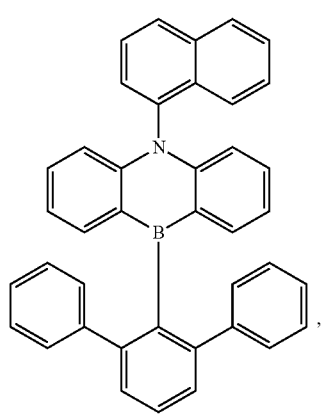
Compound 15
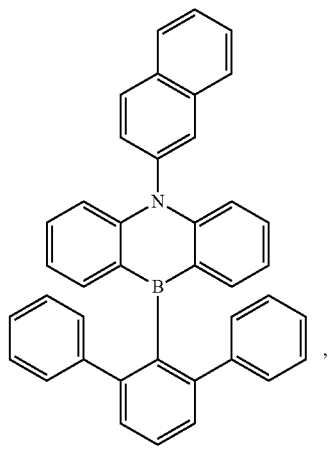
Compound 18
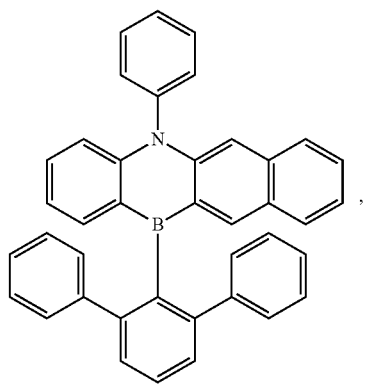
Compound 19

Compound 20
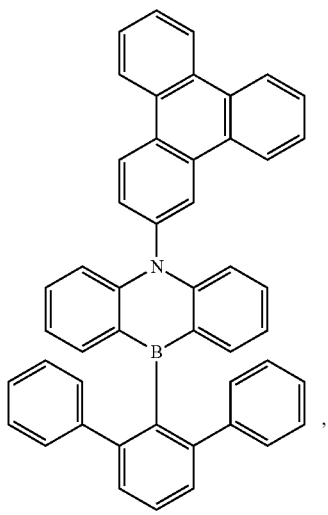
Compound 21
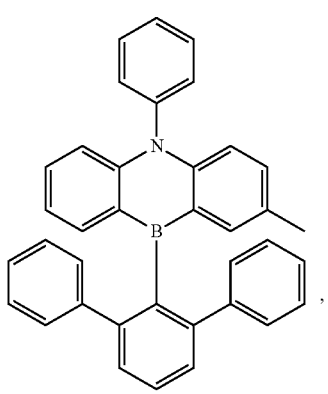
Compound 22
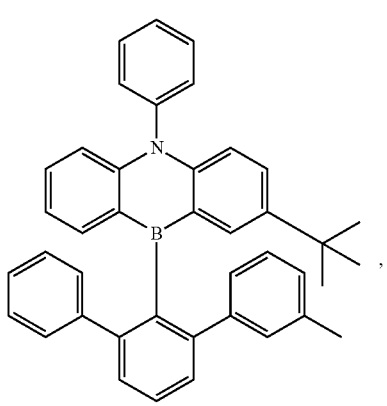
Compound 23
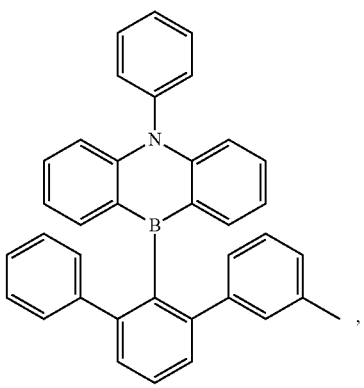
Compound 24
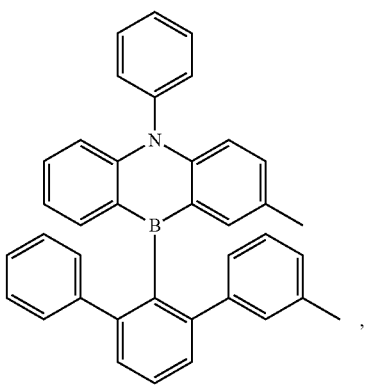
Compound 25
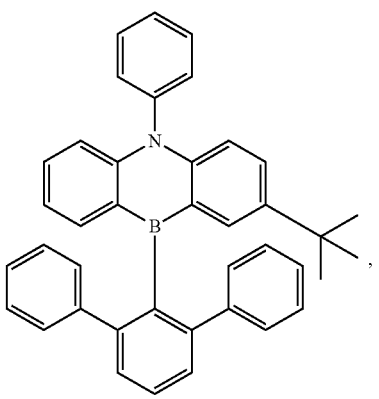

Compound 26
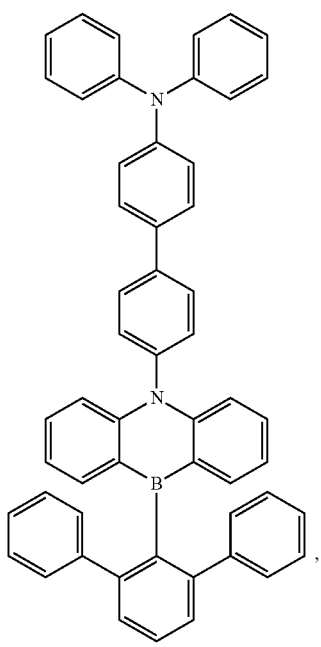
Compound 27
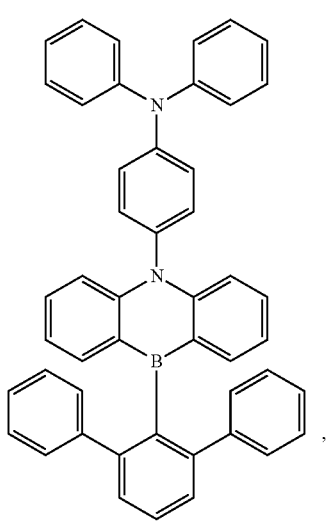
Compound 28
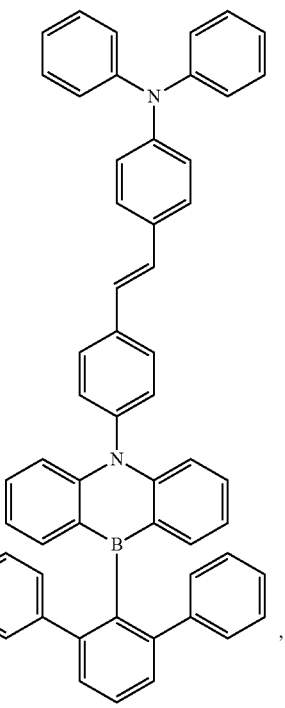
Compound 29
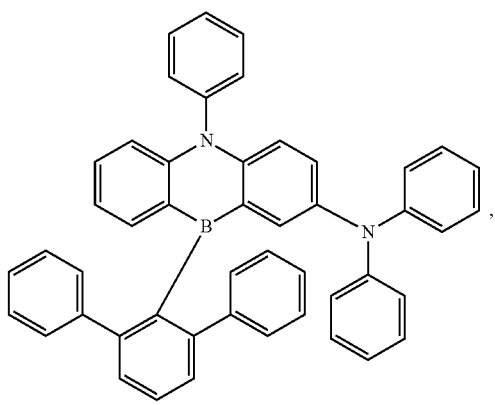
Compound 30
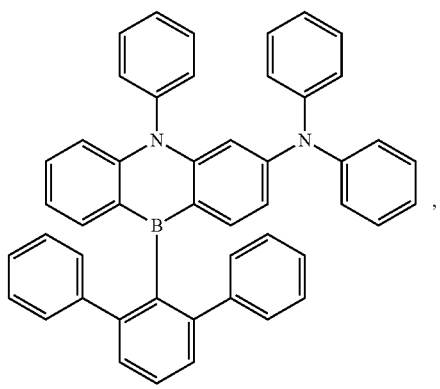

Compound 36
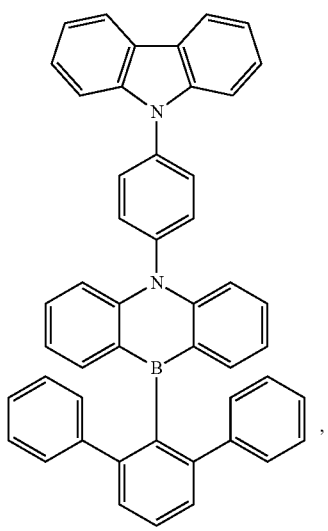
Compound 41
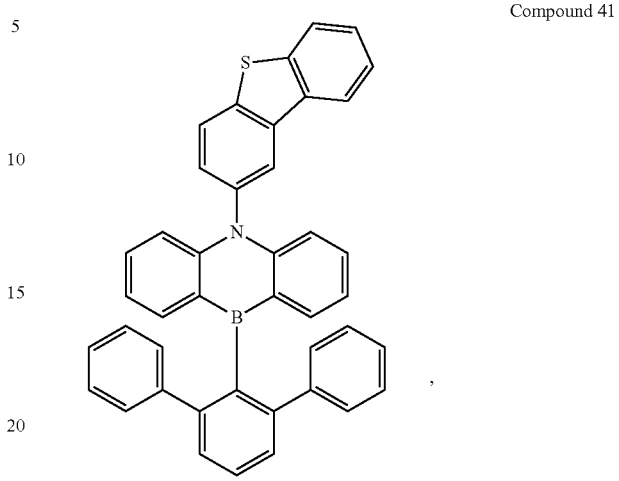
Compound 39
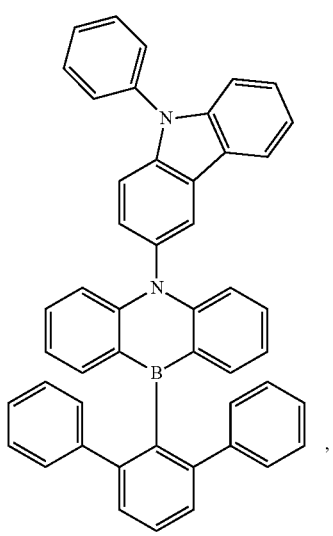
Compound 42
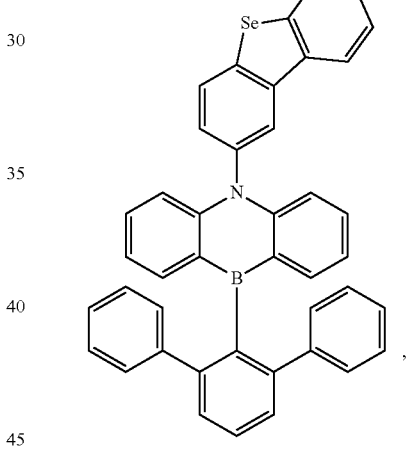
Compound 40
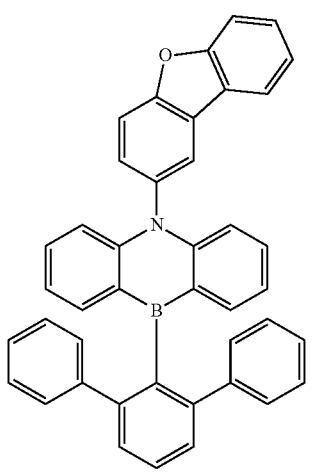
Compound 46
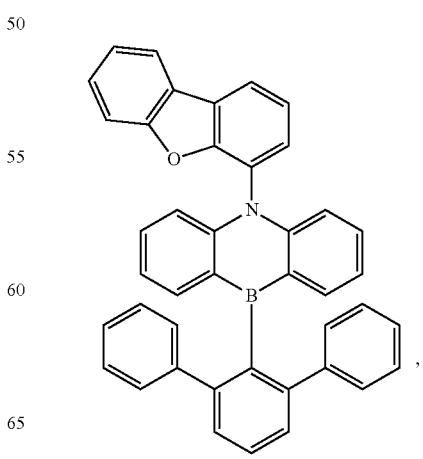

101
-continued

Compound 47

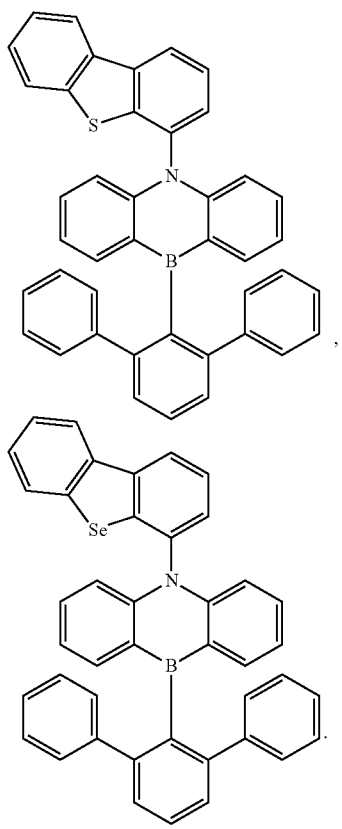
, and

Compound 48

102
-continued

Compound 55

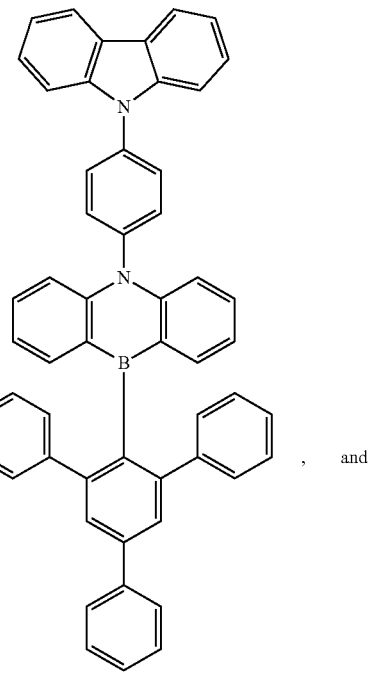
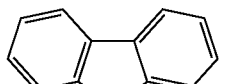
, and

Compound 59

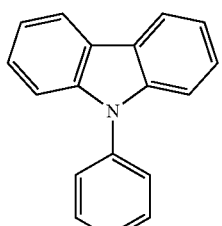

5. The compound of claim 1, wherein the compound is selected from the group consisting of:

Compound 49

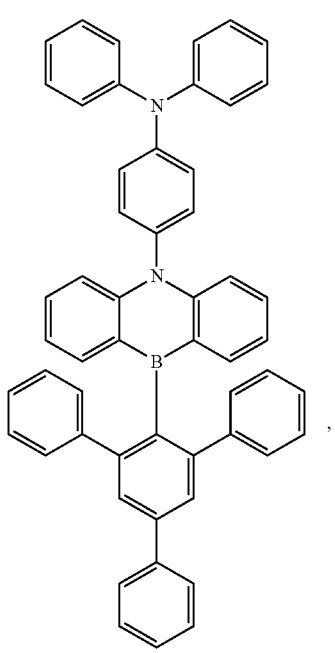
,

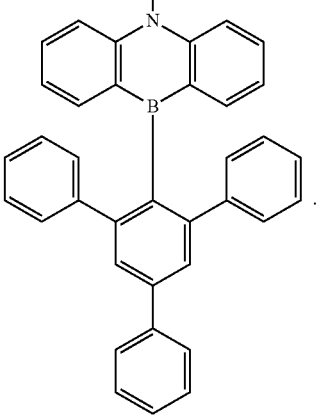
.

6. A first device comprising an organic light-emitting device, further comprising:
   an anode;
   a cathode; and
   an organic layer, disposed between the anode and the cathode, wherein the organic layer further comprises a compound comprising the formula:

Formula II

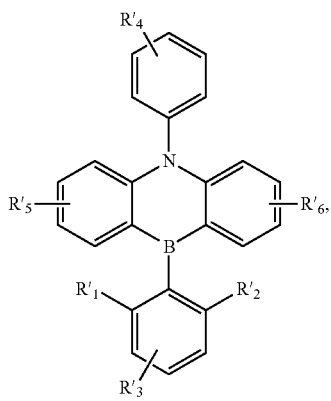

wherein R'$_4$, may represent mono, di, tri, or tetra substitutions;

wherein R'$_5$ and R'$_6$, may represent mono, di, tri, tetra, substitution;

wherein R'$_3$, may represent mono, di, or tri substitutions;

wherein R'$_1$ and R'$_2$, are independently selected from aryl and heteroaryl, wherein R'$_3$, R'$_4$, R'$_5$, and R'$_6$ are independently selected from hydrogen, alkyl, alkoxy, amino, alkenyl, alkynyl, aryl, and heteroaryl; and wherein the aryl or heteroaryl groups are conjugated or fused.

7. The first device of claim 6, wherein R'$_3$, R'$_4$, R'$_5$ and R'$_6$ are independently aryl or heteroaryl.

8. The first compound of claim 7, wherein R'$_4$ includes aryl or heteroaryl substitutions positioned ortho to the carbon atom in the phenyl group that is connected to the nitrogen atom.

9. The first device of claim 6, wherein the compound is selected from the group consisting of:

Compound 1

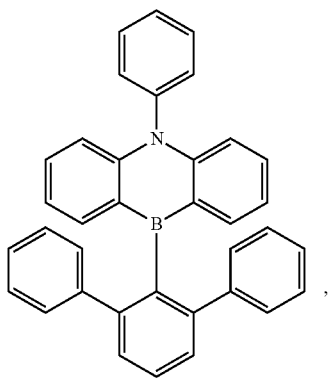

Compound 2

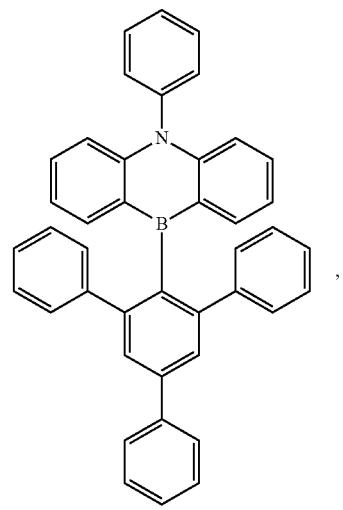

Compound 3

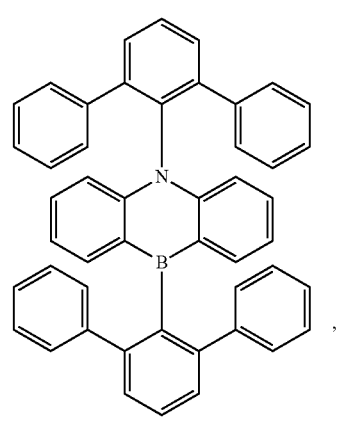

Compound 4

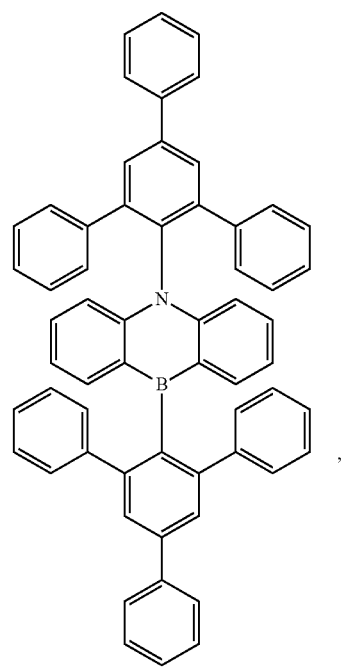

Compound 9
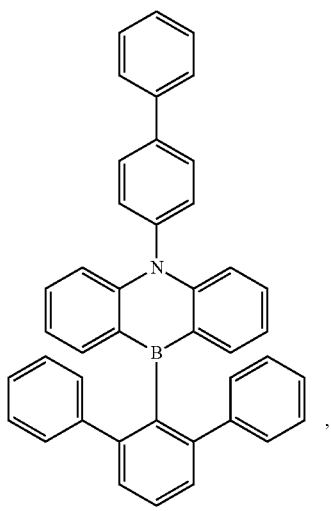
Compound 21
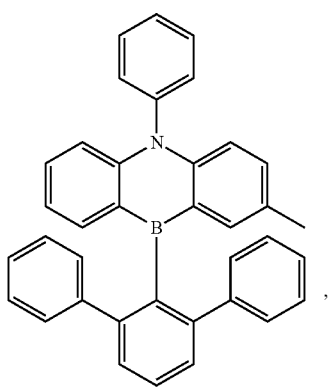
Compound 22
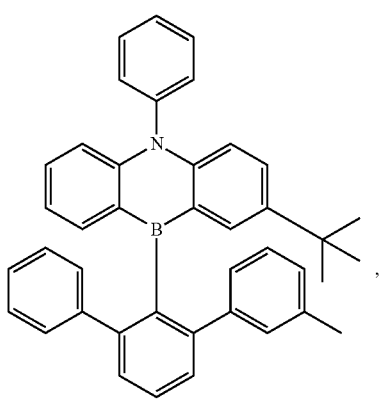
Compound 23
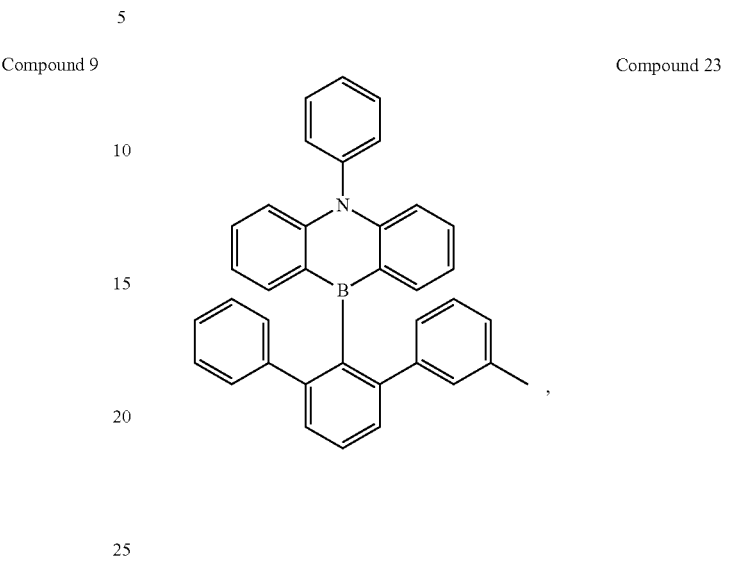
Compound 24
Compound 25
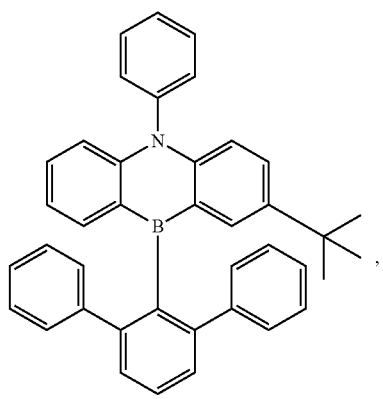

Compound 26
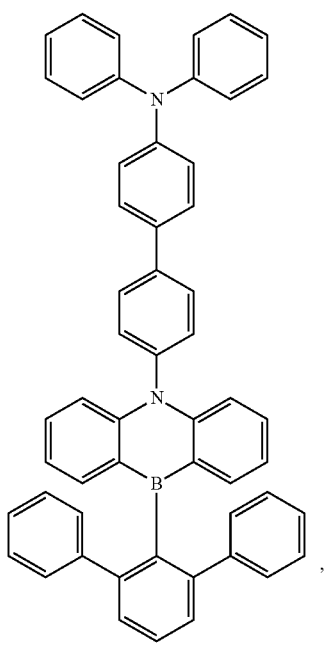
Compound 27
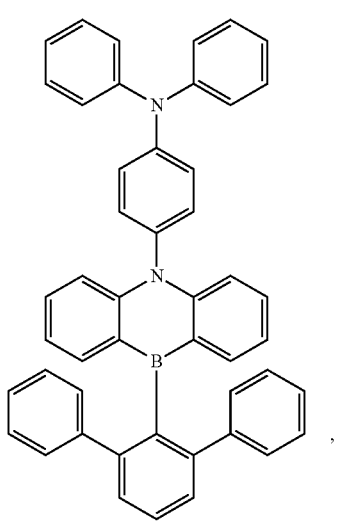
Compound 28
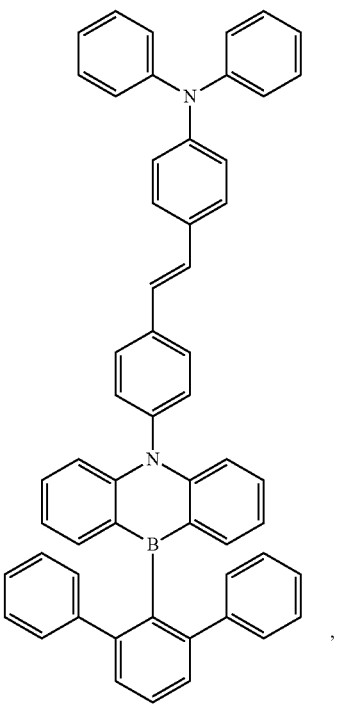
Compound 29
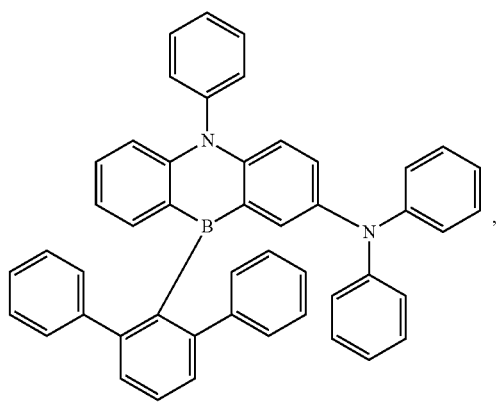
Compound 30
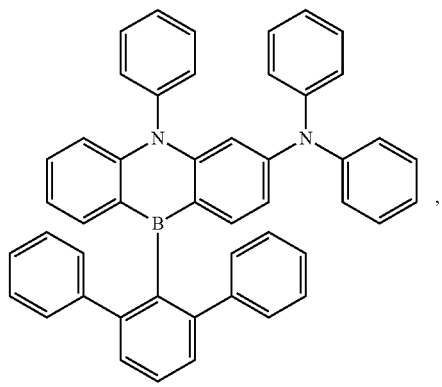

10. The device of claim 6, wherein the compound is selected from the group consisting of:

Compound 36
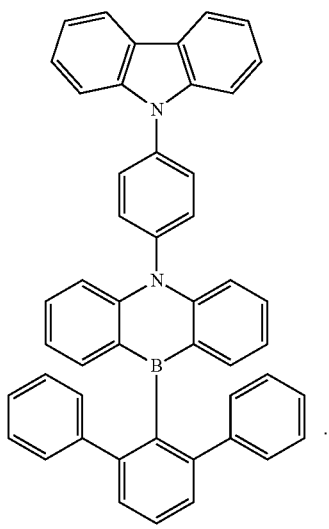

Compound 49
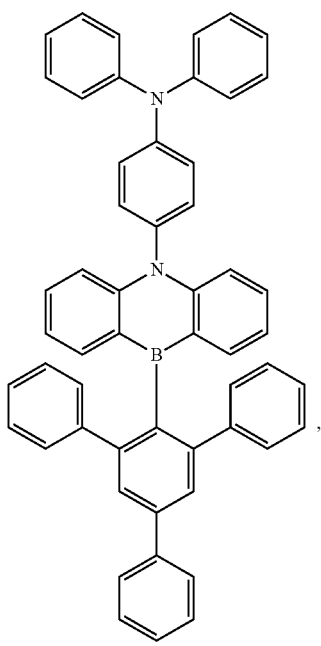

Compound 55
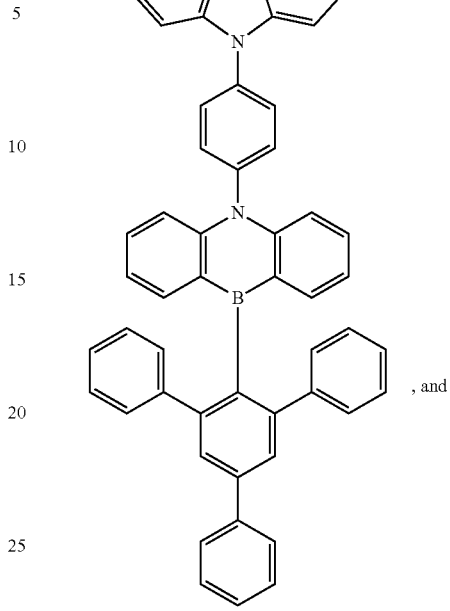

, and

Compound 59
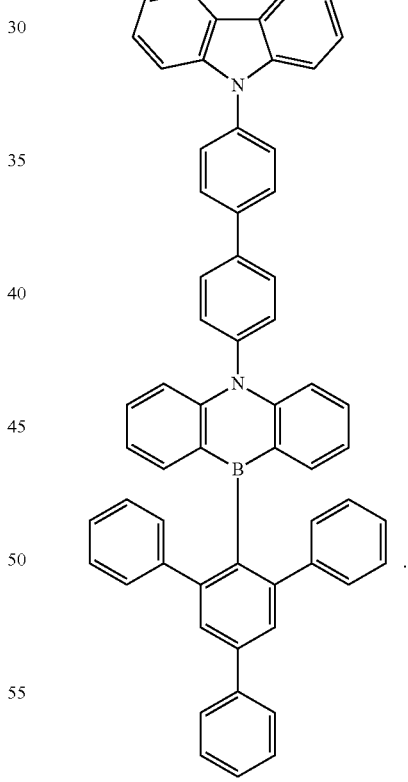

.

11. The device of claim 6, wherein the organic layer is a blocking layer and the compound having Formula II is a blocking material.

12. The first device of claim 6, wherein the organic layer is an emissive layer and the compound comprising Formula II is a host.

13. The first device of claim 12, wherein the organic layer further comprises an emissive dopant.

14. The first device of claim 6, wherein the organic layer is an emissive layer and the compound comprising Formula II is a fluorescent emitter.

15. The first device of claim 6, wherein the device is a consumer product.

16. The first device of claim 6, wherein the device is an organic light-emitting device.

17. A compound selected from the group consisting of:

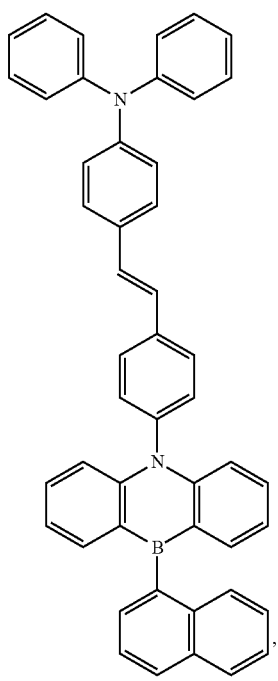

Compound 50

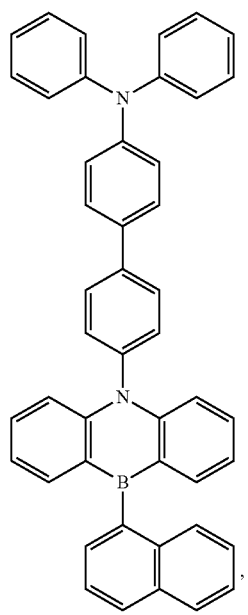

Compound 51

-continued

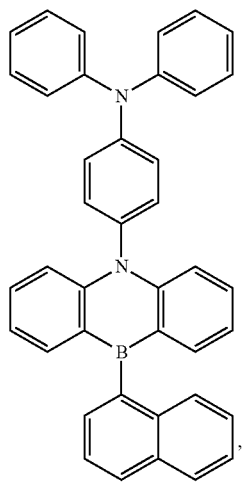

Compound 52

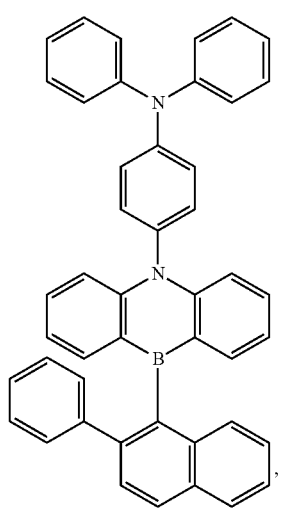

Compound 53

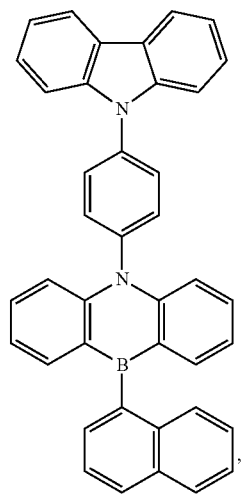

Compound 54

-continued
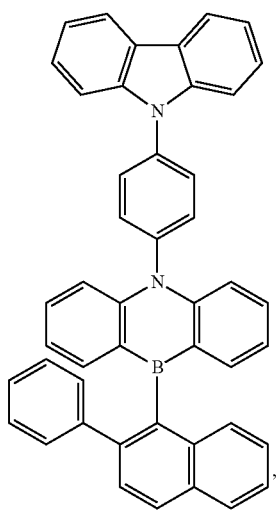
Compound 56
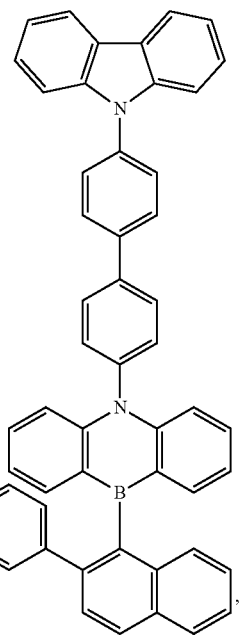
Compound 58
, and
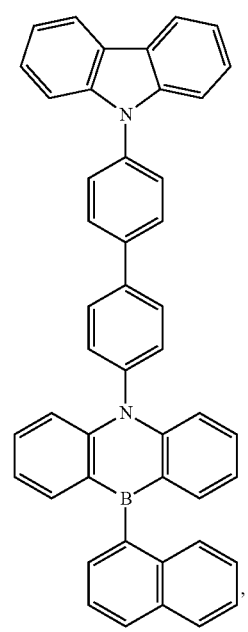
Compound 57
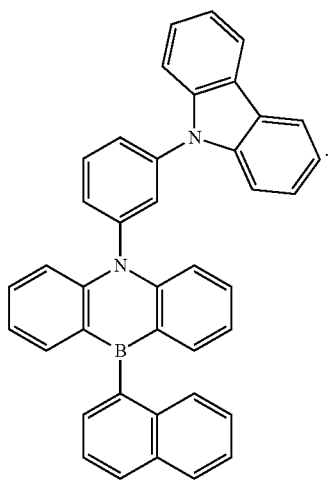
Compound 60
18. A first device comprising an organic light-emitting device, the organic light emitting device comprising:
   an anode;
   a cathode; and
   an organic layer, disposed between the anode and the cathode, wherein the organic layer further comprises at least one compound selected from the group consisting of:

Compound 50
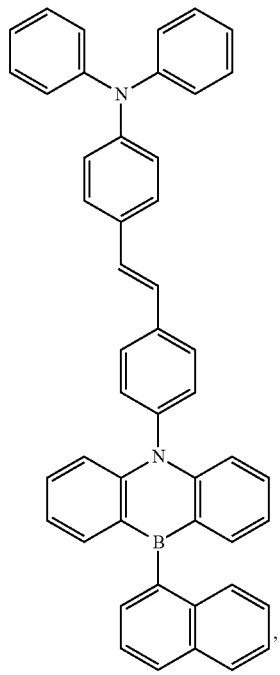
Compound 51
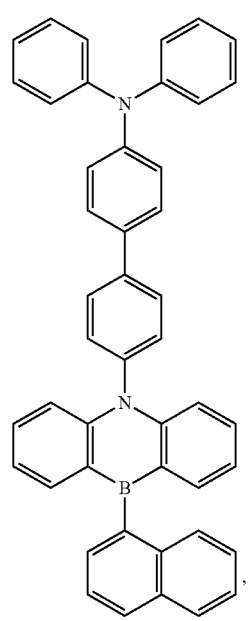
Compound 52
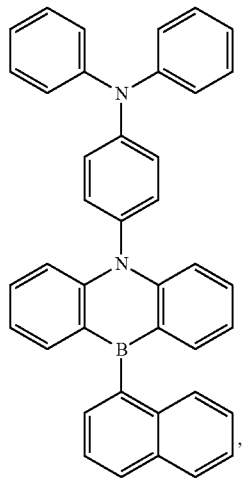
Compound 53
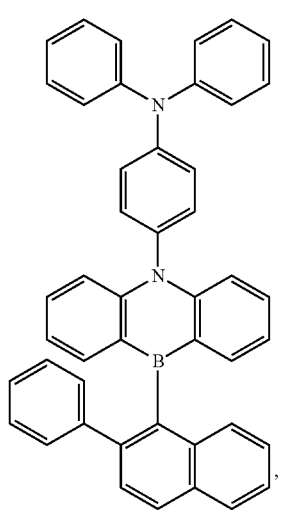
Compound 54
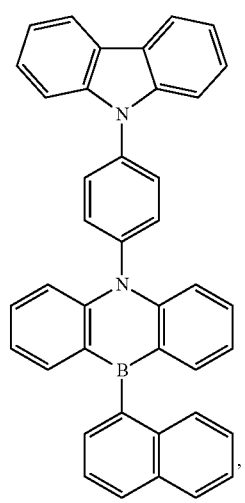

117
-continued
Compound 56
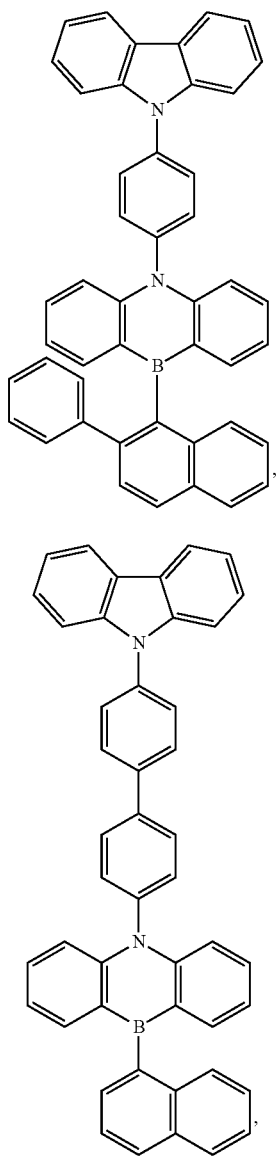
Compound 57
118
-continued
Compound 58
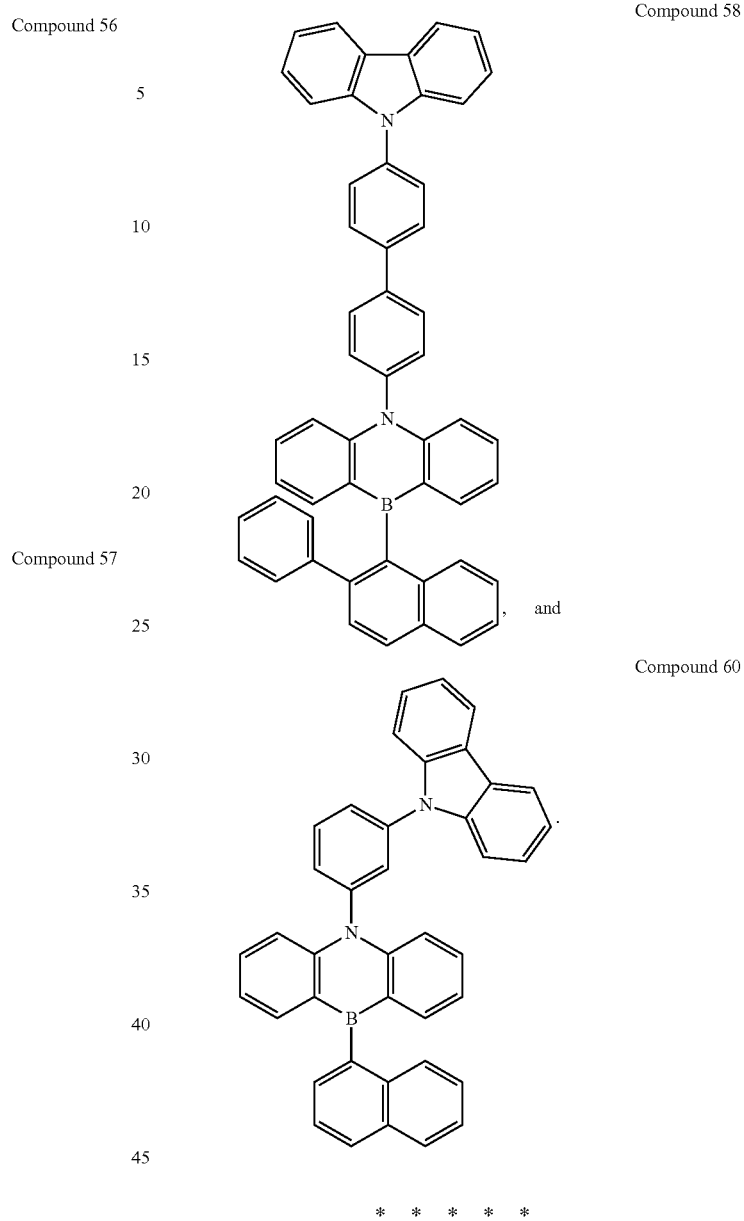
Compound 60
, and
.
* * * * *

UNITED STATES PATENT AND TRADEMARK OFFICE
CERTIFICATE OF CORRECTION

| | | |
|---|---|---|
| PATENT NO. | : 9,073,948 B2 | Page 1 of 1 |
| APPLICATION NO. | : 13/092722 | |
| DATED | : July 7, 2015 | |
| INVENTOR(S) | : Kottas | |

It is certified that error appears in the above-identified patent and that said Letters Patent is hereby corrected as shown below:

In the Claims:

Claim 8, Column 103, Line 40 delete
   "The first compound of claim 7" and input
   -- The first device of claim 7 --.

Claim 10, Column 109, Line 34 insert
   -- first -- between "The" and "device".

Claim 11, Column 110, Line 60 insert
   -- first -- between "The" and "device".

Signed and Sealed this
Ninth Day of February, 2016

Michelle K. Lee
*Director of the United States Patent and Trademark Office*